United States Patent [19]

Nakamura et al.

[11] Patent Number: 5,649,897
[45] Date of Patent: Jul. 22, 1997

[54] ENDOSCOPE APPARATUS FOR COMPENSATING FOR CHANGE IN POLARIZATION STATE DURING IMAGE TRANSMISSION

[75] Inventors: Toshihisa Nakamura; Tomohiko Hattori; Masahiro Nudeshima, all of Inokuchi Nakai-machi, Japan

[73] Assignee: Terumo Kabushiki Kaisha, Tokyo, Japan

[21] Appl. No.: 551,514

[22] Filed: Nov. 1, 1995

[30] Foreign Application Priority Data

Nov. 2, 1994 [JP] Japan ..................... 6-269914
Jan. 30, 1995 [JP] Japan ..................... 7-013103
Sep. 20, 1995 [JP] Japan ..................... 7-242195

[51] Int. Cl.⁶ ........................................ A61B 1/04
[52] U.S. Cl. .................. 600/111; 600/166; 600/117; 600/181; 600/921; 348/45
[58] Field of Search ............... 600/111, 166, 600/181, 117; 348/45, 58, 229, 687; 359/435

[56] References Cited

U.S. PATENT DOCUMENTS 4,846,154 7/1989 Macanally et al. ............ 600/171
5,222,477 6/1993 Lia .............................. 600/181 X

FOREIGN PATENT DOCUMENTS

3738667A1   5/1988   Germany .
4405102A1   8/1994   Germany .
5-67931     9/1993   Japan .
5-341207   12/1993   Japan .
WO92/19008 10/1992   WIPO .
WO94/09694  5/1994   WIPO .

*Primary Examiner*—Richard J. Apley
*Assistant Examiner*—John P. Leubecker
*Attorney, Agent, or Firm*—Burns, Doane, Swecker & Mathis, LLP

[57] ABSTRACT

An endoscope apparatus has an endoscope having an image guide (103) for guiding first and second image light components which have a parallax and can be separated from each other, a memory for storing a predetermined coefficient (a) on the basis of the shape, length, and the like of the image guide, and CCDs for converting the first and second image light components into first and second image signals (A, B). The apparatus performs image processing for generating first and second image data (L, R) by performing proportional distribution processing of the first and second image signals in accordance with the predetermined coefficient.

29 Claims, 21 Drawing Sheets

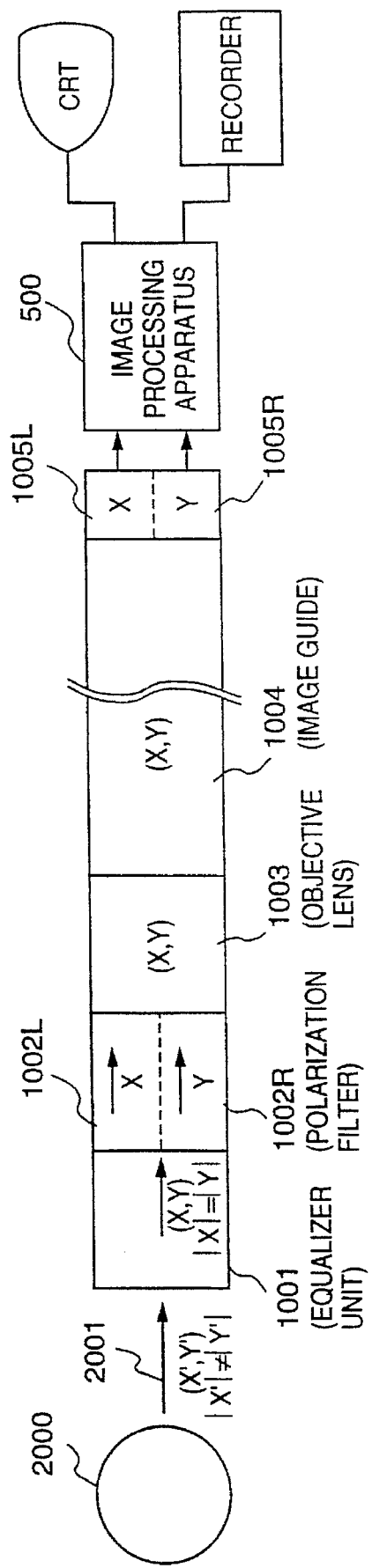

ENDOSCOPE APPARATUS FOR COMPENSATING FOR CHANGE IN POLARIZATION STATE DURING IMAGE TRANSMISSION

BACKGROUND OF THE INVENTION

The present invention relates to an image processing system for an endoscope which allows stereoscopic viewing using a monocular lens, an endoscope system which performs image processing of an image from the endoscope to visually display the image, and a method of controlling the endoscope.

Since an image obtained by a conventional monocular endoscope does not allow easy recognition of, e.g., the relative distance between a plurality of objects to be observed due to its insufficient information in the depth direction, operation errors often occur in an operation while observing the image via the endoscope. Since an operator must concentrate in order to avoid such operation errors, he or she suffers considerable fatigue both mentally and physically.

In order to solve the above-mentioned problems, stereoscopic endoscopes that allow stereoscopic viewing have been developed. In most stereoscopic endoscopes, stereoscopic images are fetched using binocular observation lenses, and are transmitted to a stereoscopic image output device via two different optical systems, thus displaying the stereoscopic images.

However, in the endoscope that allows stereoscopic viewing, since the binocular optical lenses and the two different optical systems are juxtaposed, the outer diameter of the stereoscopic endoscope increases, thus disturbing a decrease in diameter of the endoscope.

As a method of solving the problem of an increase in outer diameter, Japanese Patent publication for opposition No. 5-67931 discloses a method of transmitting parallax images within a single optical path by using a pair of polarization filters which have different azimuth angles of polarization. More specifically, the pair of polarization filters are attached to a pair of observing lenses respectively in this conventional endoscope. The pair of polarization filters generate a pair of polarized images having a parallax. A half prism combines the pair of polarized images into a single optical path to propagate within the endoscope by using polarization preservation fiber. The two polarized light images are image-sensed time-divisionally or time-parallelly to be converted into video output signals, which are input to a stereoscopic image display device. An observer observes an image on the display device as a stereoscopic image.

Two problems are posed when an image obtained by the monocular observation lens is converted into two polarized light images using the binocular polarization filters and the two polarized light images are guided in one light transmission system. That is, first, the axis of polarization of guided light shifts, and second, the two polarized light images suffer intensity unbalance.

The shift of the axis of polarization of guided light means that the plane of polarization of given linearly polarized light (e.g., polarized light having only an X-axis component but no Y-axis component) gradually shifts during propagation. As a result of the shift, the linearly polarized light undesirably acquires a Y-axis component, and consequently, crosstalk occurs in stereoscopic viewing. In the conventional system, the problem of the shift is solved by using expensive light transmission means such as a polarization holding fiber.

The intensity unbalance between two polarized light images as the second problem occurs for the following reason. That is, object light from an observation object is naturally polarized by the surface state or material of the object. The stereoscopic endoscope using the monocular observation lens can obtain a satisfactory stereoscopic image under the condition that the two polarized light components in light incident on the observation lens have equal intensities. However, as described above, when the polarization state of the object light itself is offset (for example, if the two axes of polarization are represented by X and Y, the intensity of a polarized light component X is higher than that of the polarized light component Y), the incident light itself onto the observation lens has polarization characteristics. As a result, when the pair of polarization filters are set in advance so that one of the filters transmits only polarized light X (left-eye image light) and the other filter transmit only polarized light Y (right-eye image light), the two polarized light images obtained from these filters suffer intensity unbalance (the intensity of the left-eye image light is higher than that of the right-eye image light).

SUMMARY OF THE INVENTION

The present invention has been made in consideration of the above situation, and has as its object to provide an image processing apparatus for an endoscope, which can generate image data based on image light components free from a change in polarization state from two image light components whose polarization states have changed during transmission via a single optical system, whereby, for example, an inexpensive optical fiber can be used in the endoscope.

In order to achieve the above object, according to the present invention, an image processing apparatus for an endoscope having an optical system for transmitting first and second image light components, which have a parallax and can be separated from each other, comprises:

conversion means for converting the first and second image light components into first and second image signals; and generation means for generating first and second image data by executing proportional distribution processing of the first and second image signals in accordance with a predetermined coefficient.

While two polarized light components are transmitted through an optical system, their planes of polarization shift. In this case, when the plane of polarization of one polarized light component shifts, the polarized light component acquires a polarized light component of the other polarized light component. Similarly, when the plane of polarization of the other polarized light component shifts, the other polarized light component acquires a polarized light component of the one polarized light component. Such a change in polarization state is mainly determined by the shape (e.g., the length, curvature, and diameter) and material of the optical system. Thus, a coefficient is determined on the basis of the shape of the optical system, and the first and second image signals (normally, output electrical signals from image pickup elements such as CCDs) are proportionally distributed in accordance with the predetermined coefficient so as to generate first and second image data. As a result, these image data exhibit values approximate to those of image data obtained from image data based on image light components which are free from any change in polarization state. Therefore, when this image processing apparatus is used, expensive means such as a polarization holding fiber need not be used in the endoscope.

It is another object of the present invention to provide an endoscope system which can precisely split two polarized light images obtained from an endoscope having a single optical system which allows a change in polarization state of image light during transmission.

In order to achieve the above object, according to the present invention, an endoscope system comprises:

an endoscope having an optical system for transmitting first and second image light components, which have a parallax and can be separated from each other;

conversion means for converting the first and second image light components into first and second image signals; and generation means for generating first and second image data by executing proportional distribution processing of the first and second image signals in accordance with a predetermined coefficient.

More specifically, this endoscope system can provide a system which can generate two image data which are precisely split based on two image light components (suffering a shift of their planes of polarization) of an endoscope having an inexpensive optical system without requiring any polarization holding fiber.

It is still another object of the present invention to provide a control method of an endoscope which can precisely split two polarized light images from an endoscope using an inexpensive optical system.

In order to achieve the above object, according to the present invention, a method of controlling an endoscope having an optical system for transmitting first and second image light components, which have a parallax and can be separated from each other, comprises the steps of:

converting the first and second image light components into first and second image signals by controlling image pickup elements; and generating first and second image data by performing proportional distribution processing of the first and second image signals on the basis of conversion characteristics of the image pickup elements and a predetermined coefficient representing a shape of the optical system.

According to this control method, although the planes of polarization of two image light components obtained from an endoscope having an inexpensive optical system that does not require any polarization holding fiber shift, two image data which are obtained by precisely splitting the two image light components can be generated.

According to a preferred aspect of the present invention, the optical system has an optical fiber, and the predetermined coefficient is expressed as a function of at least one of a material, diameter, and length of the optical fiber. The rate of change in polarization state of two polarized light components in the optical system can be quantified.

According to a preferred aspect of the present invention, the predetermined coefficient is expressed as a function of at least one of the material, diameter, and length of the optical fiber, and a pressure externally applied to the optical fiber. The rate of change in polarization state of two polarized light components in the optical system can be precisely quantified.

According to a preferred aspect of the present invention, the predetermined coefficient is stored in advance in storage means as a function value defined by a shape of the optical system as a parameter. The predetermined coefficient required for executing proportional distribution processing can be easily read out, and image data can be generated efficiently.

According to a preferred aspect of the present invention, the conversion means comprises image pickup elements for converting the first and second image light components into the first and second image signals as electrical signals, and inverse conversion means for inversely converting the first and second image signals from the image pickup elements into first and second light intensity data representing light intensities. Since the outputs (normally, electrical signals) from the image pickup elements have no linear relationship with the input light intensity, high-precision proportional distribution processing cannot be executed by directly using the first and second image signals. However, when the first and second image signals are inversely converted into first and second light intensity data representing the light intensities, the proportional distribution can be performed in accordance with the predetermined coefficient.

According to a preferred aspect of the present invention, the first and second image light components in the optical system have substantially different polarization characteristics.

According to a preferred aspect of the present invention, the first and second image data are stored for the purpose of a later use or displayed, thus improving practicality.

The image processing apparatus and the control method of the present invention can be applied to various endoscopes.

For example, according to a preferred aspect of the present invention, the optical system of the endoscope comprises an optical fiber, a light input portion arranged at a distal end portion of the optical fiber, and a light output portion arranged at a proximal end portion of the optical fiber, and the light input portion comprises a pair of filters which are arranged at or near an effective center in an optical axis direction as the aperture position of the observation lens, have different azimuth angles of polarization, and are divisionally arranged on right and left regions of a surface substantially perpendicular to the optical axis. This endoscope has the arrangement shown in, e.g., FIG. 11 (to be described later), and two polarization filters can be appropriately disposed in a single fiber. Therefore, each of the pair of polarization filters of the endoscope shown in FIG. 11 has a semi-circular shape.

For example, according to a preferred aspect of the present invention, the optical system of the endoscope comprises an optical fiber, a light input portion arranged at a distal end portion of the optical fiber, and a light output portion arranged at a proximal end portion of the optical fiber, and the light output portion comprises:

polarization axis rotation means for time-divisionally rotating axes of polarization of two polarized light images transmitted through the optical fiber; and an analyzer arranged behind the polarization axis rotation means.

Such an endoscope has the arrangement shown in, e.g., FIG. 13. Although time-divisional image data are obtained, the arrangement of the light output portion can be simplified.

For example, according to a preferred aspect of the present invention, the optical system of the endoscope comprises an optical fiber, a light input portion arranged at a distal end portion of the optical fiber, and a light output portion arranged at a proximal end portion of the optical fiber, and the light output portion comprises:

a beam splitter for splitting optical paths of two polarized light images transmitted through the optical fiber; and a pair of polarization filters which respectively transmit the split polarized light images and have different azimuth angles of polarization.

Such an endoscope is one shown in, e.g., FIG. 15 (to be described later), and can obtain two time-parallel image data.

For example, according to a preferred aspect of the present invention, the optical system of the endoscope comprises an optical fiber, a light input portion arranged at a distal end portion of the optical fiber, and a light output portion arranged at a proximal end portion of the optical fiber, and the light output portion comprises a pair of polarization filters which are arranged adjacent to each other at a position near an exit of the optical fiber, and have different azimuth angles of polarization to respectively transmit two polarized light images from the optical fiber.

Such an endoscope is one shown in, e.g., FIG. 16 (to be described later), and can obtain two time-parallel image data although it has a simple arrangement.

According to a preferred aspect of the present invention, the optical system of the endoscope comprises an optical fiber, a light input portion arranged at a distal end portion of the optical fiber, and a light output portion arranged at a proximal end portion of the optical fiber, and the light output portion comprises a plurality of first polarization filters and a plurality of second polarization filters, which have different azimuth angles of polarization so as to respectively transmit two polarized light images from the optical fiber.

Such an endoscope is one shown in, e.g., FIG. 17 (to be described later), and can obtain two time-divisional image data.

According to a preferred aspect of the present invention, the endoscope comprises a light guide disposed near the optical system. This endoscope is as shown in, e.g., FIG. 19, and can assure illumination.

According to a preferred aspect of the present invention, the optical system of the endoscope comprises an optical fiber, a light input portion arranged at a distal end portion of the optical fiber, and a light output portion arranged at a proximal end portion of the optical fiber, and the light output portion comprises:
an illumination light source arranged near the light output portion; and
means for guiding illumination light from the illumination light source toward an exit side associated with polarized light images of the optical fiber,
whereby the optical fiber serves as a bidirectional optical fiber, and is used as a light guide for illuminating an object. This endoscope is as shown in, e.g., FIG. 20, 21 or 22. With this arrangement, the optical fiber can be used as a bidirectional one, and can also serve as a light guide for illuminating an object.

According to a preferred aspect of the present invention, the optical system of the endoscope comprises an optical fiber, a light input portion arranged at a distal end portion of the optical fiber, and a light output portion arranged at a proximal end portion of the optical fiber, and the optical system further comprises an image reflection member at a distal end of the light input portion. This endoscope has the arrangement as shown in, e.g., FIG. 23, and allows observations of the side surface and the upper and lower surfaces of the distal end of the light input portion.

According to a preferred aspect of the present invention, the optical system preferably comprises an imaging member such as one of a convex lens, a concave lens, a Fresnel lens, and a SELFOC lens, or a combination of a plurality of lenses.

According to a preferred aspect of the present invention, the optical system of the endoscope comprises a light transmission path consisting of a relay lens, a light input portion arranged at a distal end side of the light transmission path, and a light output portion arranged at a proximal end side of the light transmission path.

According to a preferred aspect of the present invention, the endoscoe system further comprises a pair of solid-state image pickup elements arranged behind the optical system of the endoscope.

It is still another object of the present invention to provide an endoscope which can satisfactorily attain stereoscopic viewing by eliminating nonuniformity of the polarization state in incident light even when incident light itself to an observation lens has polarization characteristics in a stereoscopic endoscope for transmitting right- and left-eye images using two polarized light images as two parallax images.

In order to achieve the above object, an endoscope for guiding, along a single optical path, two polarized light images obtained by splitting image light incident via an observation lens, and using the two polarized light images as two parallax images, comprises:

equalizer means, arranged in front of the observation lens, for equalizing two polarized light components in incident light; and optical means for splitting the incident light with the two equalized polarized light components into two polarized light images, whereby intensities of the two parallax images obtained from the optical means are equal to each other.

According to a preferred aspect of the present invention, the equalizer means consists of a material having optical characteristics for eliminating the polarization characteristics of the incident light.

According to a preferred aspect of the present invention, the equalizer means comprises means such as a phase shifter for rotating the polarizing angle of the incident light.

According to a preferred aspect of the present invention, the equalizer means has first and second light transmission elements having equal areas. The shift amount of the phase of the azimuth angle of polarization of transmission light by the first light transmission element is set to deviate through 90° from that by the second light transmission element. Since the two light transmission elements have equal areas, the light intensities of two polarized light components incident on optical means become equal to each other.

According to a preferred aspect of the present invention, the first light transmitting element comprises a $\lambda/2$ phase shifter, and the second light transmitting element comprises a semi-circular light transmitting plate which does not change a phase.

According to a preferred aspect of the present invention, a division line of the first and second light transmitting elements is perpendicular or parallel to a split direction of the optical means.

According to a preferred aspect of the present invention, the equalizer means comprises first and second light transmitting elements having equal areas, and a shift amount upon shifting of a phase of an azimuth angle of polarization of transmission light by the first light transmitting element is 90° out of phase from a shift amount upon shifting of a phase of an azimuth angle of polarization of transmission light by the second light transmitting element.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 1A is a diagram showing the arrangement of an endoscope system as a preferred embodiment having a polarized light intensity correction function and a polarized light shift compensation function according to the present invention;

DETAILED DESCRIPTION OF THE EMBODIMENTS

Figure 1B:
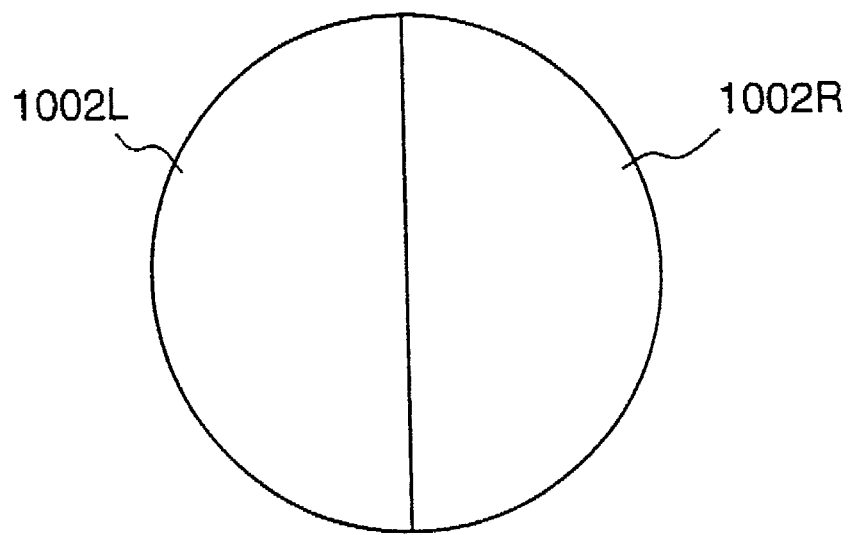
FIG. 1B is a view showing the arrangement of polarization filters used in the endoscope shown in FIG. 1A.

A stereoscopic endoscope system to which the present invention is applied will be described in detail below with reference to the accompanying drawings.

<Arrangement of Overall Endoscope System>

FIG. 1A shows the arrangement of an endoscope system having an endoscope to which the present invention is applied. In this specification, a device which includes an optical system such as an image guide, a lens, and the like, and externally outputs an image of an object 2000 present in front of the image guide will be referred to as an "endoscope" (1000 in FIG. 1A), an apparatus which obtains a visible image by processing an image signal (normally, an electrical signal) obtained by converting image light output from the endoscope will be referred to as an "image processing apparatus (500 in FIG. 1A) for the endoscope, and a system constituted by the "endoscope" and the "image processing apparatus" will be referred to as an "endoscope system".

The endoscope 1000 of this embodiment mainly has three optical systems, i.e., a light amount equalizer unit 1001, a polarization filter unit 1002, and an image guide 1004 consisting of, e.g., an optical fiber.

Reference numeral 2000 denotes an object to be observed. Reference numeral 2001 denotes light from the object. Normally, this light 2001 is polarized. Assume that the light 2001 has two polarized light components. For the sake of convenience, the two polarized light components are indicated by X' and Y', and the azimuth angles of polarization of these polarized light components are indicated by X and Y. In principle, these azimuth angles need only be different from each other, but need not always be perpendicular to each other. However, for the sake of convenience, assume that the azimuth angles are perpendicular to each other, and this relationship is expressed by X_Y.

In general, two arbitrary polarized light components in reflected light often have different intensities. Therefore, since the intensities of the above-mentioned two polarized light components X' and Y' are not equal to each other, either, this fact is expressed by |X'|≠|Y'| in FIG. 1A.

The equalizer unit 1001 comprises a phase shifter such as a half-wave plate, as will be described later, and has a function of equalizing the intensities of the two polarized light components X' and Y' to eliminate nonuniformity of the light amounts of the two polarized light components X' and Y' included in light from the above-mentioned object 2000. This fact is expressed by |X'|=|Y'|. Since the two polarized light components X and Y are superposed on each other in the equalizer unit 1001, this state is indicated by (X, Y). The equalizer unit 1001 guides light including these two polarized light components X and Y to the polarization filter unit 1002 behind the unit 1001.

The polarization filter unit 1002 splits and extracts the polarized light components X and Y from the light including the superposed polarized light components X and Y. The filter unit 1002 has two filter portions 1002L and 1002R which have the same area, as shown in FIG. 1B. The filter portion 1002L transmits only the polarized light component X, and the filter portion 1002R transmits only the polarized light component Y. Since the two filter portions 1002L and 1002R abut with each other, the polarized light component X transmitted through the filter portion 1002L becomes an image for the left eye, and the polarized light component Y transmitted through the filter portion 1002R becomes an image for the right eye.

Both the polarized light components X and Y output from the filter unit 1002 are incident on an objective lens 1003. In the objective lens 1003, the two polarized light components X and Y are superposed on each other. This state is indicated by (X, Y). The objective lens 1003 guides the two superposed, polarized light components (X, Y) to the image guide 1004. The polarized light components (X, Y) are guided to a photoelectric conversion unit 1005 along the image guide 1004. The photoelectric conversion unit 1005 splits and extracts these two polarized light components, and converts the split polarized light components into electrical signals.

Image signals output as electrical signals from the conversion unit 1005 are converted into image signals to be displayed on a CRT device or image signals for a recording device by the image processing apparatus 500.

When the two polarized light components X and Y are guided along the image guide 1004, their azimuth angles of polarization shift. Due to this shift, when the two polarized light components are incident on the photoelectric conversion unit 1005, the polarized light component X as the image for the left eye has a Y-direction component and the polarized light component Y as the image for the right eye has an X-direction component. Therefore, a photoelectric converter 1005L detects the image for the left eye mixed with the image for the right eye, and a photoelectric converter 1005R detects the image for the right eye mixed with the image for the left eye. The image processing apparatus 500 performs image processing for compensating for this crosstalk phenomenon.

Note that the endoscope system shown in FIG. 1A has a basic arrangement. Therefore, the arrangement has various variations. For example, the polarization filter unit 1002 is disposed in front of the objective lens 1003 in FIG. 1A, but may be disposed behind the lens 1003.

Various embodiments of the endoscope system according to the present invention will be described in detail below.

<First Embodiment>

Figure 2:
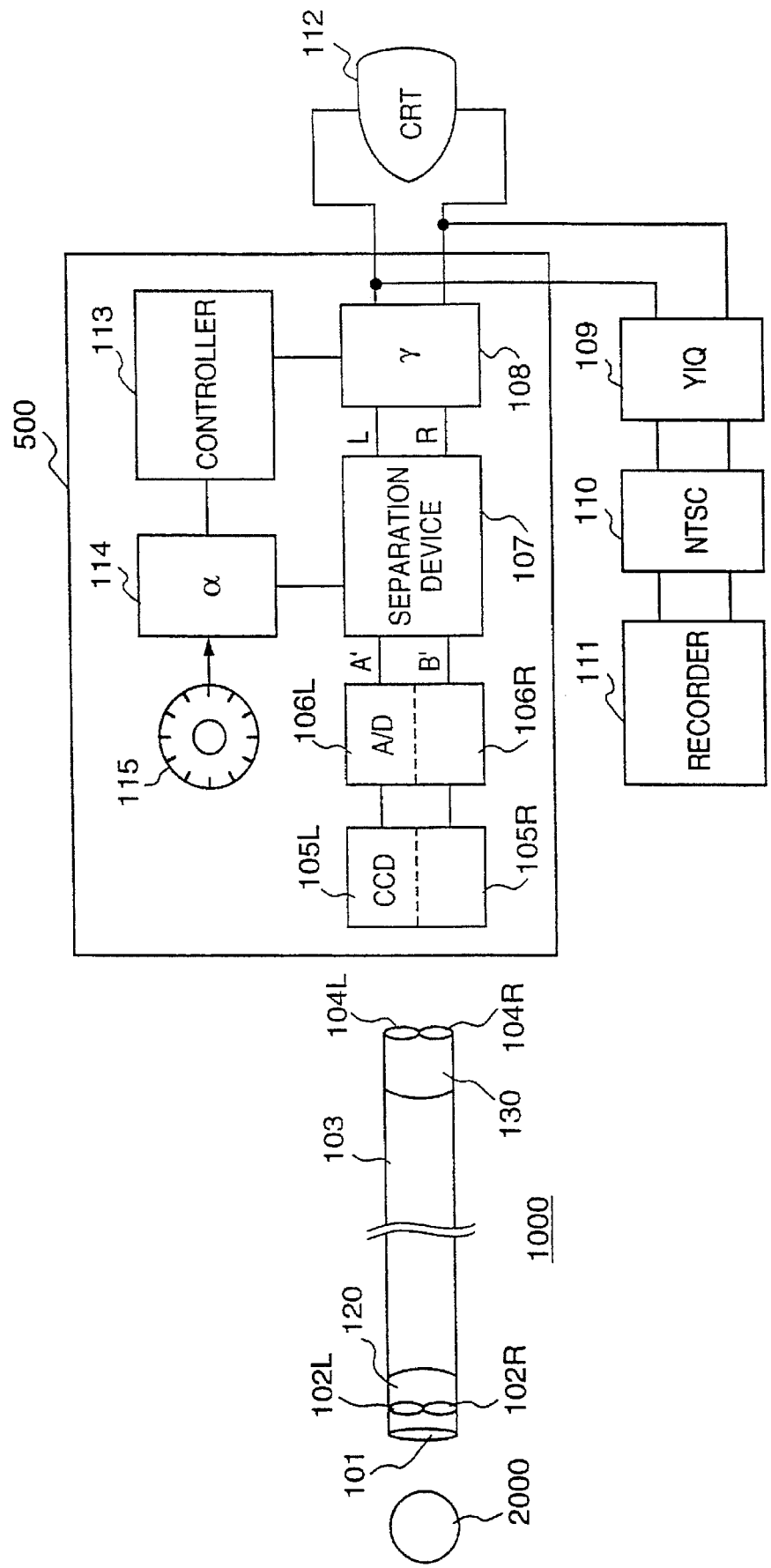
FIG. 2 is a diagram showing the arrangement of an endoscope apparatus (endoscope system) according to the first embodiment of the present invention.

FIG. 2 shows the arrangement of an endoscope apparatus (endoscope system) according to the first embodiment.

Referring to FIG. 2, reference numeral 1000 denotes an endoscope; 2000, an object to be observed; and 500, an image processing apparatus. As described above, the image processing apparatus 500 performs image processing for solving the problem of the shift of the axis of polarization of polarized light guided in the endoscope. The endoscope 1000 shown in FIG. 2 has a special phase shifter 101 for solving the problem of intensity nonuniformity of two polarized light components included in image light incident into the endoscope 1000. The phase shifter 101 corresponds to the equalizer unit 1001 in the system shown in FIG. 1A.

Reference numeral 103 denotes an image guide comprising a single optical fiber. The system shown in FIG. 2 guides an image of an intracorporeal portion 2000 of a patient extracorporeally via the guide 103. The image signals of this image are processed by the image processing apparatus 500, are displayed on a CRT 112, and (or) are stored in a recorder 109 in the NTSC format.

Figure 6:
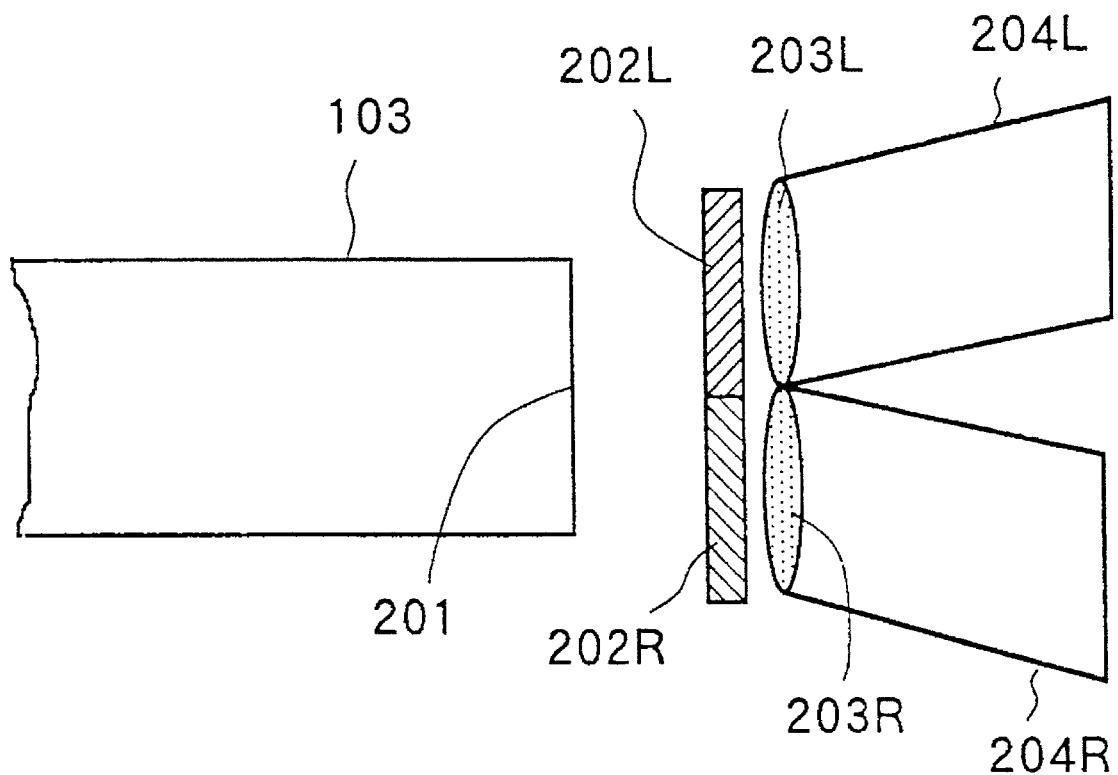
FIG. 6 is a view showing the arrangement of a light output portion of the endoscope shown in FIG. 2.

A light input portion 120 is arranged on one end of the guide 103, and a light output portion 130 is arranged on the other end of the guide 103. The arrangement of the light input portion 120 is shown in detail in FIGS. 3 and 4, and the arrangement of the light output portion 130 is shown in FIG. 6.

The light input portion 120 has the phase shifter 101 for correcting any nonuniformity of the intensities of two polarized light components in incident light, and two polarization filters 102L and 102R for splitting image light transmitted through the phase shifter 101 into image light for the left eye and image light for the right eye. The filters 102L and 102R respectively split a light component polarized in the X-direction (to be referred to as an X-polarized light component hereinafter for the sake of simplicity) from the object 2000 to be observed, and a light component polarized in the Y-direction (the Y-direction is perpendicular to the X-direction, and this light component will be referred to as a Y-polarized light component hereinafter for the sake of simplicity), and guide the light components into the guide 103. These polarized light components are guided along the guide 103, and reach analyzers 104L and 104R in the light output portion 130. The X-polarized light (image for the left eye) and the Y-polarized light (image for the right eye) split by the analyzers 104L and 104R are respectively converted by CCDs 105L and 105R into electrical signals, which are converted into digital image signals A' and B' by A/D converters 106L and 106R. Note that each CCD has R, G, and B filters (not shown), and hence, each of these digital signals A' and B' has R, G, and B components. A separation device 107 extracts image signals L and R for the left and right eyes generated via the analyzers 104L and 104R from the digital image signals A' and B' to be separated from each other. A γ correction device 108 corrects the signals L and R to match human's eyes.

When the image signals L and R are to be observed on the CRT 112, the image signals are displayed on the CRT 112 via a stereoscopic image controller 113. On the other hand, when the image signals L and R are stored in the recorder 111, the signals L and R in the RGB format are converted into signals of a YIQ system by a circuit 109, and the converted signals are converted into the NTSC format by a circuit 110.

Figure 3:
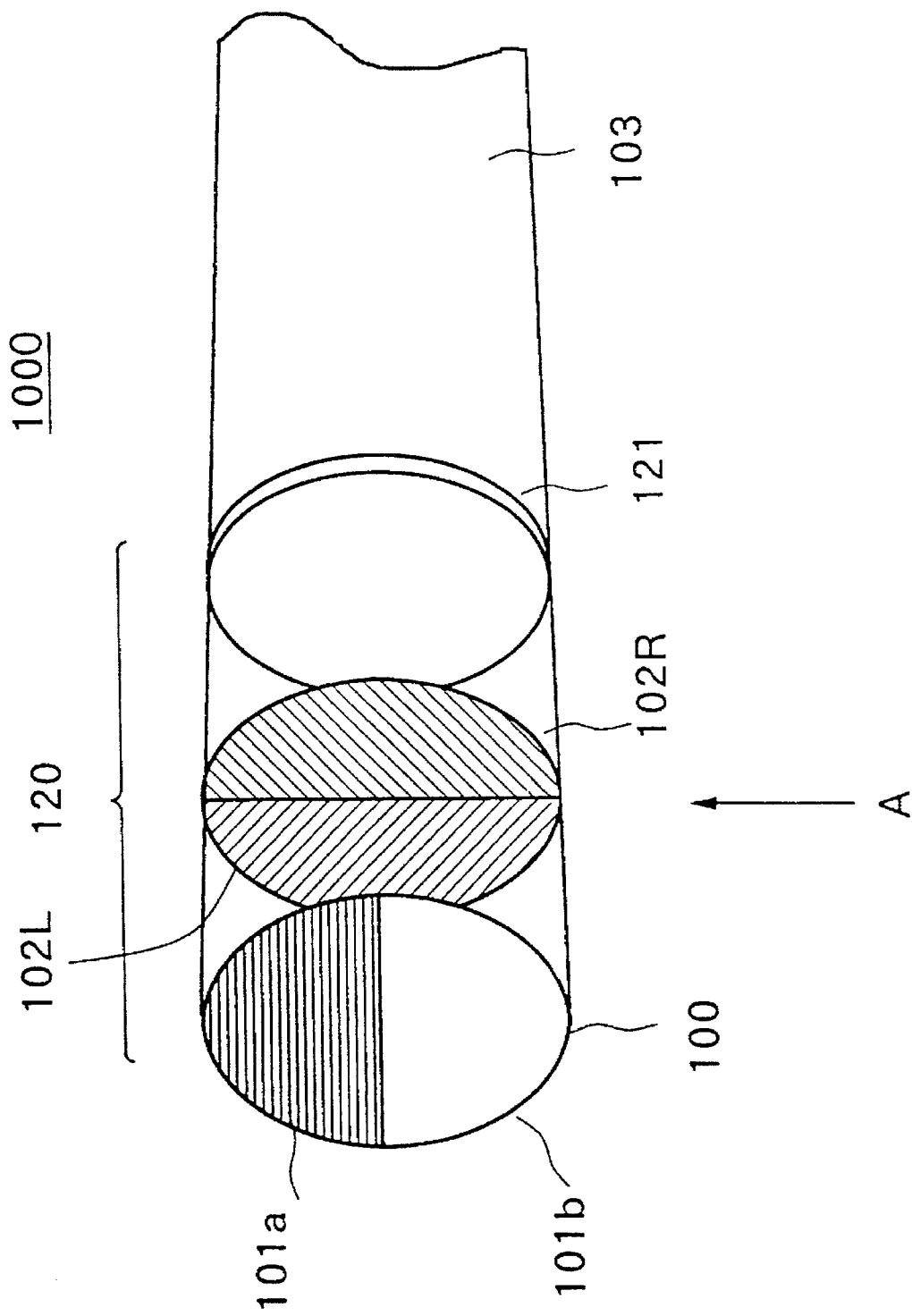
FIG. 3 is a view showing the arrangement of a light input portion of the endoscope of the embodiment shown in FIG. 2.
Figure 4:
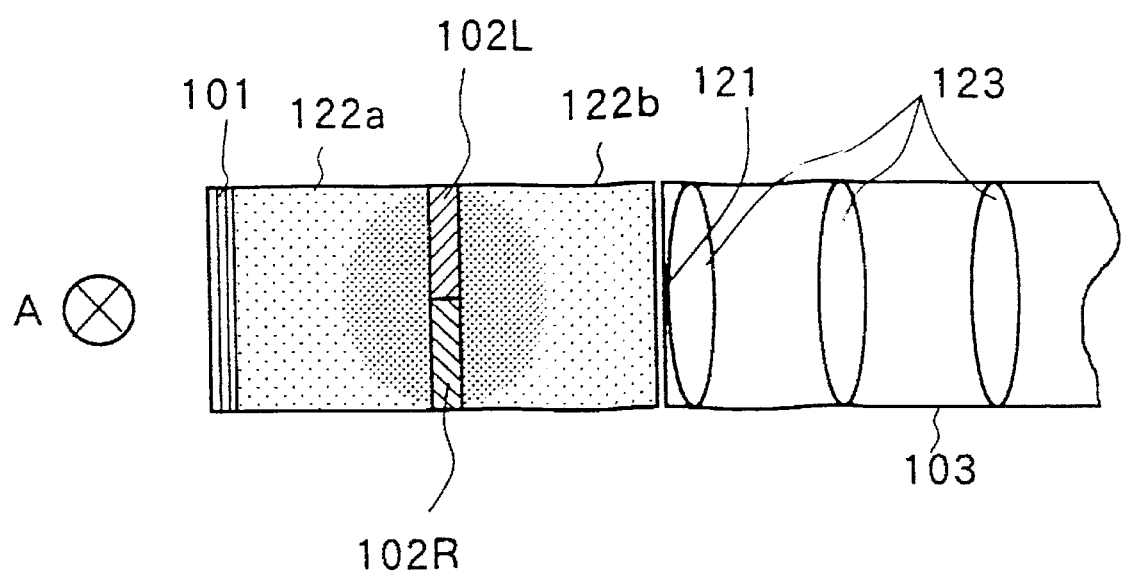
FIG. 4 is a sectional view showing the arrangement of a light input portion of the endoscope of the embodiment shown in FIG. 1.

FIGS. 3 and 4 show the arrangement of the light input portion 120. In FIGS. 3 and 4, behind the phase shifter 101, the filters 102L and 102R which have two planes of polarization split in the direction of an arrow A in FIG. 4, and a GRIN (gradation index) lens 122a inserted between the phase shifter 101 and the filters 102L and 102R are arranged. Also, a GRIN lens 122b is inserted behind the filters 102L and 102R. More specifically, the pair of polarization filters 102L and 102R are sandwiched between the GRIN lenses 122a and 122b. The polarization filters 102L and 102R are located at or near the effective center of the aperture of the GRIN lens 122a. The azimuth angles of polarization of the pair of polarization filters 102L and 102R are respectively right angles. For the sake of convenience, the azimuth angle of polarization of the polarization filter 102L will be referred to as an X-direction hereinafter, and the azimuth angle of polarization of the polarization filter 102R will be referred to as a Y-direction hereinafter. The pair of polarization filters 102L and 102R are disposed by dividing a horizontal surface perpendicular to the optical axis into left and right regions. A light input surface 121 of the image guide 103 is arranged on a surface on which the image of an object is substantially formed by the GRIN lenses 122a and 122b.

In place of the GRIN lens 122, a convex lens, a Fresnel convex lens, a combination of a plurality of lenses, or the like may be used. In FIG. 4, the image guide 103 has a relay lens group 123. In place of the lens group 123, the image guide 103 may be constituted by an optical fiber.

The pair of polarization filters 102L and 102R have equal areas, as described above. Therefore, if the X-axis component of polarized light incident on the filter 102L for the left eye is equal to the Y-axis component of polarized light incident on the filter 102R for the right eye, the intensity of the X-polarized light incident on the GRIN lens 122b via the filter 102L becomes equal to the intensity of the Y-polarized light incident on the GRIN lens 122b via the filter 102R. However, as described above, the intensities of X- and Y-polarized light components included in light reflected by the object 2000 are normally not equal to each other. The phase shifter 101 equalizes the X- and Y-polarized light components included in the object light from the object 2000, and inputs the equalized light components to the pair of polarization filters 102L and 102R. More specifically, the phase shifter 101 serves as an intensity equalizer (i.e., the equalizer unit 1001 shown in FIG. 1A).

Figure 5A:
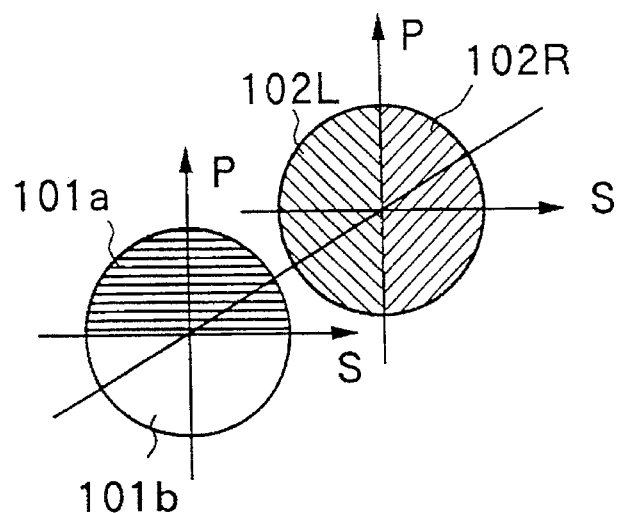
FIG. 5A is a view showing an example of the relationship between the directions of polarization of a phase shifter 101 and a polarization filter 101 in the light input portion shown in FIG. 3.

The arrangement and operation of the phase shifter 101 will be explained below with reference to FIG. 5A. Referring to FIG. 5A, the phase shifter 101 has a region 101a for rotating the plane of polarization of incident light by 90 degrees and a region 101b for transmitting light without rotating the plane of polarization. The areas of the regions 101a and 101b of the phase shifter 101 are equal to each other. Therefore, when arbitrarily polarized light (its azimuth angle of polarization is represented by W and its intensity is represented by I) is incident on the phase shifter 101 (its area is represented by S), light emerging from the region 101a having an area S/2 has an azimuth angle of W+90° (its intensity is I/2), and is incident on the polarization filters 102 in this state. On the other hand, light emerging from the region 101b having an area S/2 has an azimuth angle of W° (its intensity is I/2), and is similarity incident on the polarization filters 102. As described above, since the polarization filters 102L and 102R have a 90° difference between their azimuth angles of polarization, even when the azimuth angle W is arbitrary, the light intensity of the X-direction component transmitted through the polarization filter 102L becomes equal to that of the Y-direction component transmitted through the polarization filter 102R.

In this manner, the intensities of the two polarized light components that reach the analyzers 104L and 104R are adjusted to become equal to each other. Therefore, independently of the polarization state of light from the object 2000, the intensity of light (image light for the left eye) transmitted through the filter 102L becomes equal to that of light (image light for the right eye) transmitted through the filter 102R. Hence, the intensity nonuniformity is eliminated by the phase shifter 101.

Figure 5B:
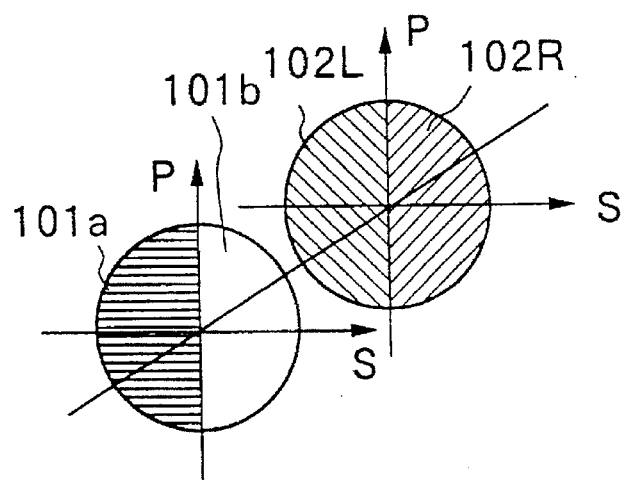
FIG. 5B is a view showing another example of the relationship between the directions of polarization of the phase shifter 101 and the polarization filter 101 in the light input portion shown in FIG. 3.
Figure 5C:
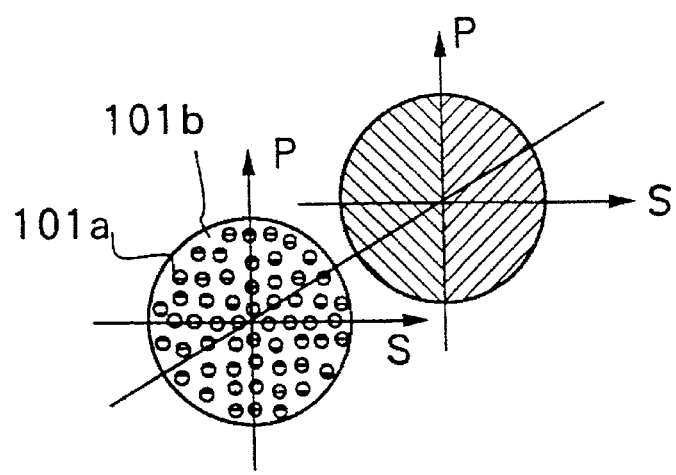
FIG. 5C is a view showing still another example of the relationship between the directions of polarization of the phase shifter 101 and the polarization filter 101 in the light input portion shown in FIG. 3.

FIGS. 5B and 5C respectively show modifications of the disposition of the phase shifter 101 shown in FIG. 5A.

More specifically, in the phase shifter 101 of the modification shown in FIG. 5B, the division line for dividing the regions 101a and 101b in the phase shifter 101 is set to be parallel to the division line for dividing the polarization filters 102L and 102R.

In the modification of FIG. 5C, the phase shifter 101 is constituted by a plurality of small phase shifter pieces 101a each having a function of shifting the azimuth angle of polarization of transmitted light through 90°, and a plurality of small transmitting pieces 101b which do not have the above-mentioned function (transmitting the light). In this case, the total area of the plurality of phase shifter pieces 101a is set to be equal to that of the plurality of transmitting pieces 101b.

In the examples shown in FIGS. 5A to 5C, the polarization filters 102L and 102R are perpendicular to each other. The present invention is not limited to such filters 102.

The phase shifter 101 shown in FIGS. 5A to 5C partially rotates the polarizing angle of incident light. In place of the phase shifter 101 for rotating the axis of polarization, the phase shifter 101 may consist of a material which cannot hold the polarization state of incident light, i.e., a material in which the azimuth angle of polarization of polarized light transmitted therethrough shifts gradually, thus also achieving the object of the present invention. More specifically, when such a material is used, the plane of polarization of light transmitted through the phase shifter 101 varies, and hence, the intensities of light components transmitted through the filters 102L and 102R become equal to each other.

Figure 7:
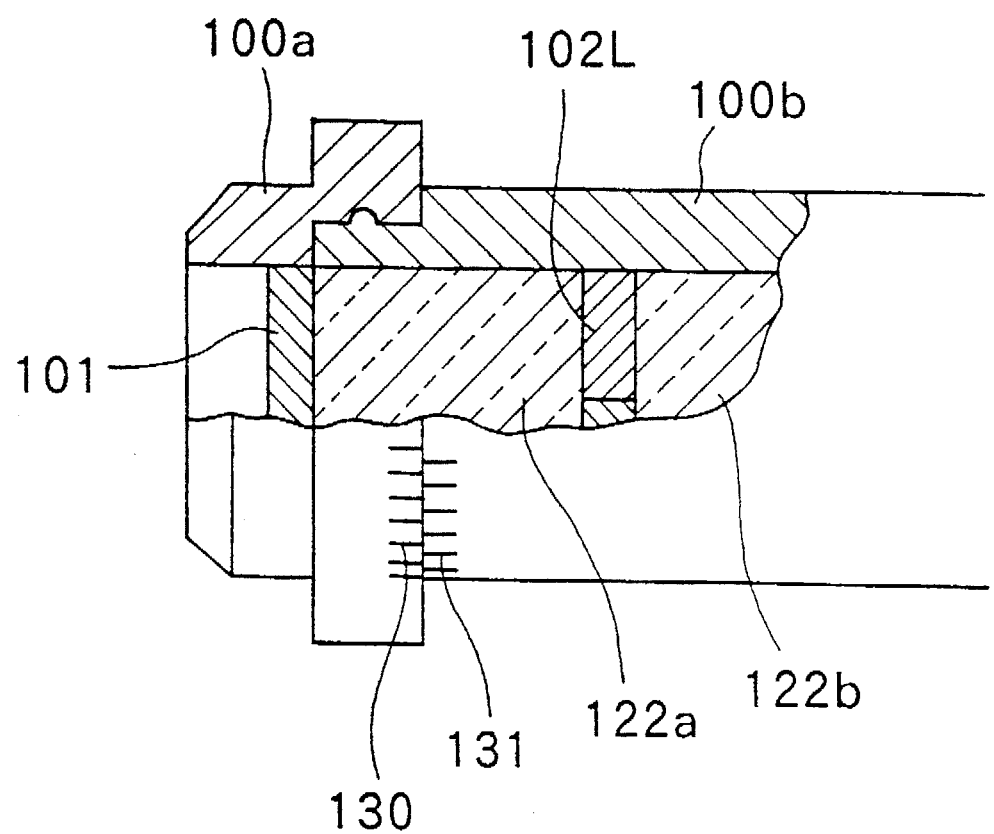
FIG. 7 is a partially cutaway sectional view showing the internal structure of the endoscope shown in FIG. 2.

FIG. 7 is a partially cutaway sectional view of the light input portion 120 shown in FIG. 4. Referring to FIG. 7, the light input portion 120 is constituted by lens barrels 100a and 100b. The phase shifter 101 is held by the outer barrel 100a, and the lenses 122 and the polarization filters 102 are held by the inner barrel 100b. As has been described above with reference to FIGS. 5A to 5C, the rotation angle about the optical axis of the phase shifter 101 is important. Thus, in FIG. 7, the rotation position of the phase shifter 101 is adjustable. In FIG. 7, reference numerals 130 and 131 denote scales making the rotation angle.

FIG. 6 shows the arrangement of the light output portion 130 of the endoscope of this embodiment.

More specifically, reference numeral 201 denotes a light output surface of the guide 103; and 202 (202L and 202R), polarization filters (corresponding to 104 in FIG. 2). The polarization filters 202L and 202R are juxtaposed next to each other, so that light transmitted through the guide 103 is incident on the filters 202L and 202R. Television cameras 204L and 204R are respectively disposed behind the filters 202L and 202R.

With this disposition, the two polarized light components guided along the image guide 103 are split by the filters 202L and 202R, and are converted into electrical signals by the CCDs 105 (FIG. 2) via an imaging lens 203.

The polarizing angle of polarized light incident on the image guide 103 via the light input portion 120 shifts during propagation in the image guide 103. As described above, this shift generates crosstalk of images to be displayed for the right and left eyes. The image processing apparatus 500 performs image processing for preventing this crosstalk. The principle of preventing crosstalk is as follows.

Light from the object 2000 includes various polarized light components, and is imaged on the filters 102 via the imaging lens (GRIN lens) 122a. As described above, the filters 102L and 102R respectively split X- and Y-polarized light components of the various polarized light components and guide the split light components into the image guide. Therefore, the image light L for the left eye as X-polarized light, and the image light R for the right eye as Y-polarized light are superposed on each other in the image guide. Since the X- and Y-polarized light components are perpendicular to each other, they can be split by the analyzers 104L and 104R in principle. However, in practice, since the polarizing angles of both the X- and Y-polarized light components as the image light components for the left and right eyes disperse during transmission in the image guide 103, the polarized light wavefronts of polarized light images split by the analyzers 104L and 104R shift gradually. More specifically, the X-polarized light component (Y-polarized light component) as image light for the left (right) eye from the polarization filter 102L (102R) is linearly polarized light in the X-direction (Y-direction) immediately after it emerges from the polarization filter 102L (102R), but its plane of polarization shifts during propagation, and the linearly polarized light acquires a Y-polarized light component (X-polarized light component). In other words, the analyzer 104L for detecting an image for the left eye detects an X-polarized light component from the polarization filter 102L and an X-polarized light component which is generated due to the shift of the Y-polarized light component from the polarization filter 102R and causes crosstalk. Similarly, the analyzer 104R for detecting an image for the right eye detects a Y-polarized light component from the polarization filter 102R, and a Y-polarized light component which is generated due to the shift of the X-polarized light component from the polarization filter 102L and causes crosstalk. As a result, the image signal for the left eye detected by the analyzer 104L is mixed with the image signal for the right eye, and the image signal for the right eye detected by the analyzer 104R is mixed with the image signal for the left eye. The above-mentioned separation device 107 simply separates the image signals for the right and left eyes.

Figure 8:
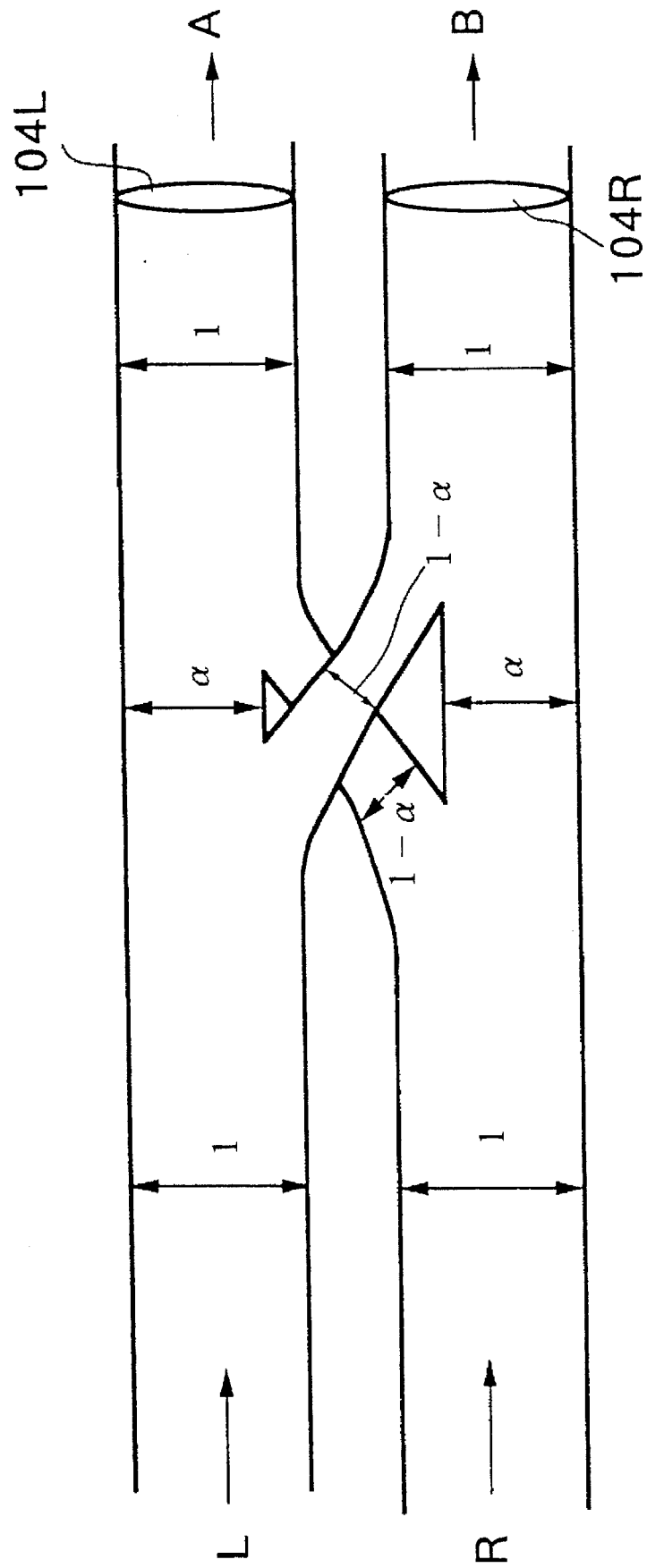
FIG. 8 is a view for explaining the principle of splitting two polarized light components in the first embodiment of the present invention.

FIG. 8 shows the mixing state of light components in the image guide 103. FIG. 8 illustrates polarized light L (X-polarized light) and polarized light R (Y-polarized light) to be separated from each other. However, in practice, the polarized light components L and R are "superposed" on each other since they are waves.

Let A be the polarized light split by the analyzer 104L, and B be the polarized light split by the analyzer 104R. Assuming that light behaves like particles in the guide 103 using an optical fiber, the polarized light L is superposed on the polarized light R by (1-a)%, and (1-a)% (a is the ratio at which the image guide 103 maintains the polarization state of light passing therethrough) of the polarized light R is superposed on the polarized light L. As can be seen from FIG. 8, A and B are respectively expressed by:

$$A = a \cdot R + (1-a) \cdot L \quad (1)$$

$$B = a \cdot L + (1-a) \cdot R \quad (2)$$

for $0 \leq a \leq 1$, and $a \neq 0.5$, and a is the characteristic determined by the material, M, and the number, N, of various optical elements (e.g., lens 122) in the optical system used in the image guide 103, the propagation distance, LTH, from the polarization filter 102 to the analyzer 104, and the pressure acting on the image guide 103.

Therefore, from equations (1) and (2), L and R are respectively given by:

$$L = \frac{A \cdot a}{2a-1} - \frac{B \cdot (1-a)}{2a-1} \quad (3)$$

$$R = \frac{B \cdot a}{2a-1} - \frac{A \cdot (1-a)}{2a-1} \quad (4)$$

The light components A and B are those incident on the CCDs 105L and 105R, and signals input to the separation device 107 are the electrical signals A' and B' from the CCDs 105L and 105R. In general, the intensity of light incident on the CCD does not have a linear relationship with the output voltage. Therefore, the output voltages A' and B' from the A/D converters 106L and 106R cannot be directly used in calculating equations (3) and (4).

Figure 9:
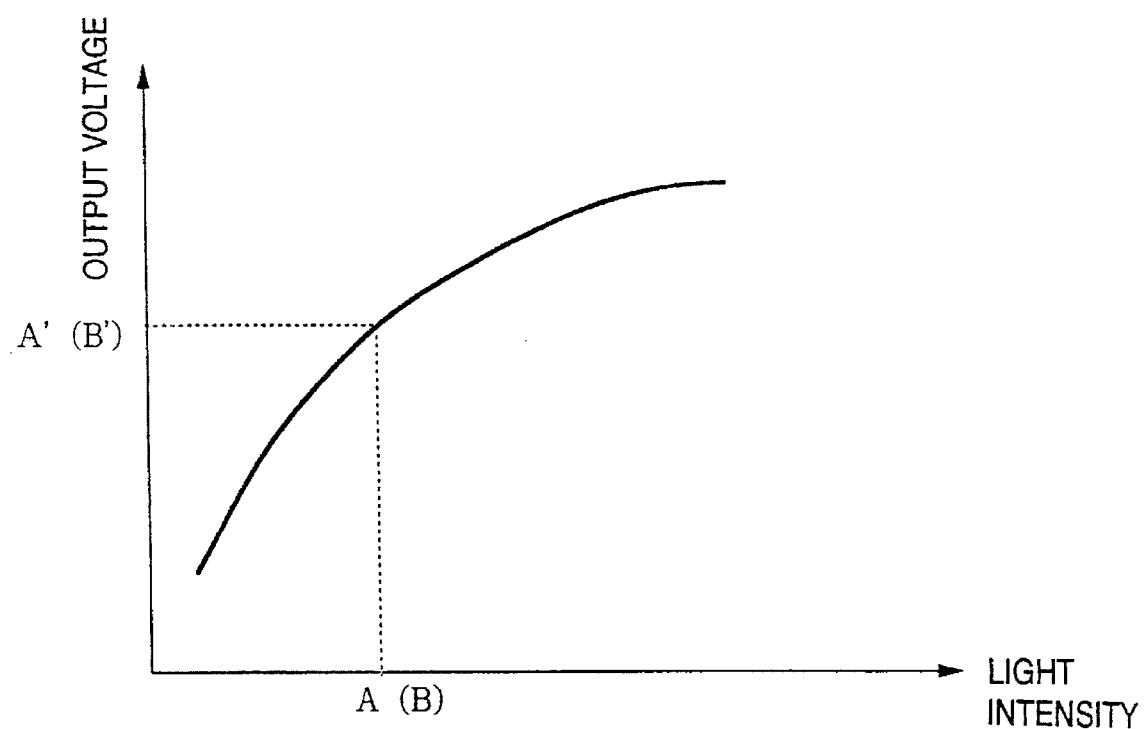
FIG. 9 is a graph for explaining the principle of photo-electric conversion in the embodiment.

FIG. 9 shows the relationship between the incident light A on the CCD and the output voltage A' from the CCD. Since this relationship is known, the incident light intensities A and B on the CCDs 105L and 105R can be estimated on the basis of the relationship shown in FIG. 9 if the output voltages A' and B' from the CCDs 105L and 105R can be measured. The separation device 107 separately extracts the polarized light components L and R quantitatively by substituting the incident light intensities A and B in equations (3) and (4).

In practice, when the separation device 107 comprises a ROM or table for outputting the inverse conversion result shown in FIG. 9 and the calculation results of equations (3) and (4), a compact apparatus and high-speed processing are realized. Equations (1) and (2) imply that if the ratio of maintaining the polarization state is defined by the weighting coefficient a with respect to a bundle $\phi$ of light rays transmitted through the lens barrel, the bundle can be distributed to a bundle (a·$\phi$) of light rays whose polarization state can be maintained, and a bundle (1−a·$\phi$) of light rays whose polarization state cannot be maintained. Therefore, the calculations according to equations (3) and (4) will be referred to as "weighted difference" (or proportional distribution) hereinafter.

The coefficient a is stored in advance in a storage device 114 in FIG. 2. A user inputs the material M and the number N of optical elements in the optical system, the propagation distance LTH, and the like via a predetermined user interface. The controller 113 searches the storage device 114 on the basis of the above-mentioned values, and reads out a target value a from the storage device 114.

For example, when the image guide 103 comprises a quartz optical fiber, a is 0.73 if the guide 103 has a diameter I of 0.7 mm and a length LTH of 2 m, and the pressure P is 1 atm. On the other hand, when the fiber is a plastic fiber consisting of, e.g., PMMA, polystyrene, polycarbonate, or the like, a is 0.6 if the guide has I of 1.0 mm and a length LTH of 2 m, and the pressure P is 1 atm.

Like in the system shown in FIG. 2, when the system has a display device such as the CRT 112, a user can visually observe an image sensed by this endoscope. In this case, the user changes the value a by operating a dial switch 115 while observing the image on the CRT 112 so as to attain the best stereoscopic viewing.

Note that the CCDs 105L and 105R may have linear output characteristics depending on the light intensity values of incident light. If the intensity of a polarized light image falls with the range that guarantees the linearity of the CCD 105, the inverse conversion can be omitted.

<Second Embodiment>

Various endoscope systems of the present invention will be proposed below by describing an endoscope system according to the second embodiment of the present invention.

Figure 10:
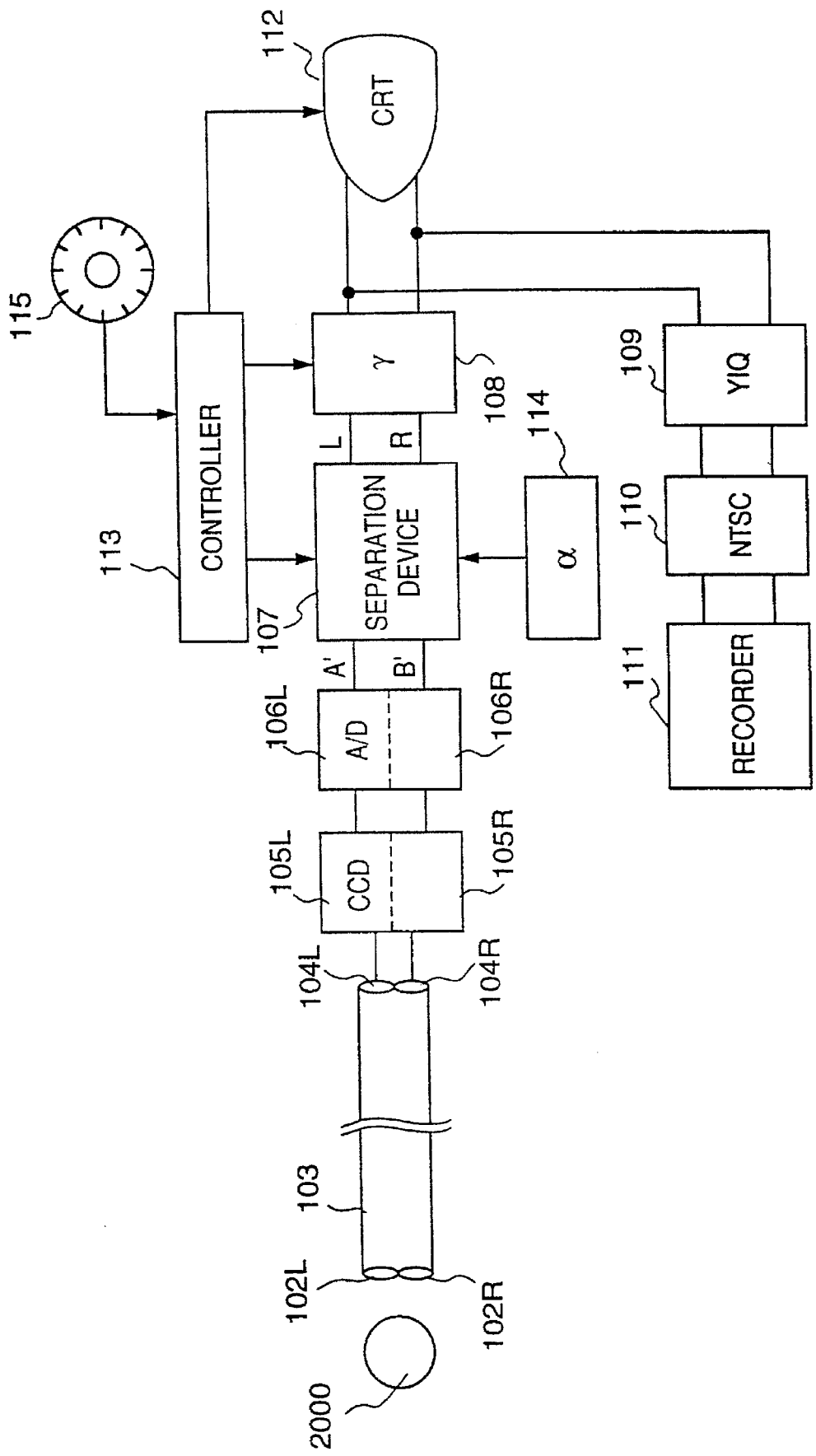
FIG. 10 is a diagram showing the arrangement of an endoscope system according to the second embodiment of the present invention.

FIG. 10 shows the arrangement of the endoscope system of the second embodiment. In the system of the second embodiment, the arrangement of an endoscope 1000 is simplified by removing the light amount equalizer unit 1001 from the endoscope 1000 shown in FIG. 1A.

Referring to FIG. 10, reference numeral 103 denotes an image guide comprising a single optical fiber. The system shown in FIG. 10 guides an image of an intracorporeal portion 2000 of a patient extracorporeally via the guide 103, and displays the image on a CRT 112 and (or) stores the image in a recorder 111 in the NTSC format.

An imaging optical system (not shown) is arranged on one end of the guide 103, and two polarization filters 102L and 102R are also arranged. The filters 102L and 102R respectively split light polarized in the X-direction (to be referred to as X-polarized light hereinafter for the sake of simplicity) from the object 2000 to be monitored, and light polarized in the Y-direction (the Y-direction is perpendicular to the X-direction, and this polarized light will be referred to as Y-polarized light hereinafter for the sake of simplicity), and guide the split light components into the guide 103. These polarized light components are guided in the guide 103 and reach analyzers 104L and 104R. The X-polarized light (an image for the left eye) and the Y-polarized light (an image for the right eye) split by the analyzers 104L and 104R are respectively converted into electrical signals by CCDs 105L and 105R, and the electrical signals are respectively converted into digital image signals A' and B' by A/D converters 106L and 106R. Note that each CCD has R, G, and B filters (not shown), and hence, each of these digital signals A' and B' has R, G, and B components. A separation device 107 extracts image signals L and R for the left and right eyes generated via the analyzers 104L and 104R from the digital image signals A' and B' to be separated from each other. A γ correction device 108 corrects the signals L and R to match human's eyes.

When the image signals L and R are to be observed on the CRT 112, the image signals are displayed on the CRT 112 via a stereoscopic image controller 113. On the other hand, when the image signals L and R are stored in the recorder 111, the signals L and R in the RGB format are converted into signals of a YIQ system by a circuit 109, and the converted signals are converted into the NTSC format by a circuit 110.

As described above, in the guide 103, the image light L as the X-polarized light and the image light R as the Y-polarized light are mixed. Since the X- and Y-polarized light components are perpendicular to each other, they can be split by the analyzers 104L and 104R in principle. However, in practice, since the polarizing angles of both the X- and Y-polarized light components as the image light components for the left and right eyes disperse during transmission in the image guide 103, the polarized light wavefronts of polarized light images split by the analyzers 104L and 104R shift gradually. More specifically, the plane of polarization of the X-polarized light shifts, and the polarized light acquires a Y-polarized light component. On the other hand, the plane of polarization of the Y-polarized light shifts, and the polarized light acquires an X-polarized light component. As a result, the image signal for the right eye is mixed in the image signal for the left eye detected by the analyzer 104L, and the image signal for the left eye is mixed in the image signal for the right eye detected by the analyzer 104R. The above-mentioned separation device 107 simply separates the image signals for the right and left eyes.

Thus, in the endoscope 1000 of the second embodiment, crosstalk is prevented using the separation device 107 for performing image processing according to equations (3) and (4) like in the first embodiment.

As in the first embodiment, the CCDs 105L and 105R may have linear output characteristics depending on the light intensity values of incident light. If the intensity of a polarized light image falls within the range that guarantees the linearity of the CCD 105, the inverse conversion can be omitted.

<Other Examples of Endoscope>

A plurality of endoscopes according to modifications other than the first and second embodiments of the endoscope which requires the separation device 107 shown in FIGS. 2 and 10 will be explained below. In these modifications, the arrangement of the endoscope is changed variously. In the endoscope of each of these modifications, two polarized light components propagate while mixing with each other.

<Arrangement of Endoscope> . . . First Example

The system shown in each of FIGS. 2 and 10 parallelly (simultaneously) obtains images for the right and left eyes. The first example uses a single polarization filter and time-divisionally outputs X- and Y-polarized light components while the systems shown in FIGS. 2 and 10 use the two polarization filters 102L and 102R.

Figure 11:
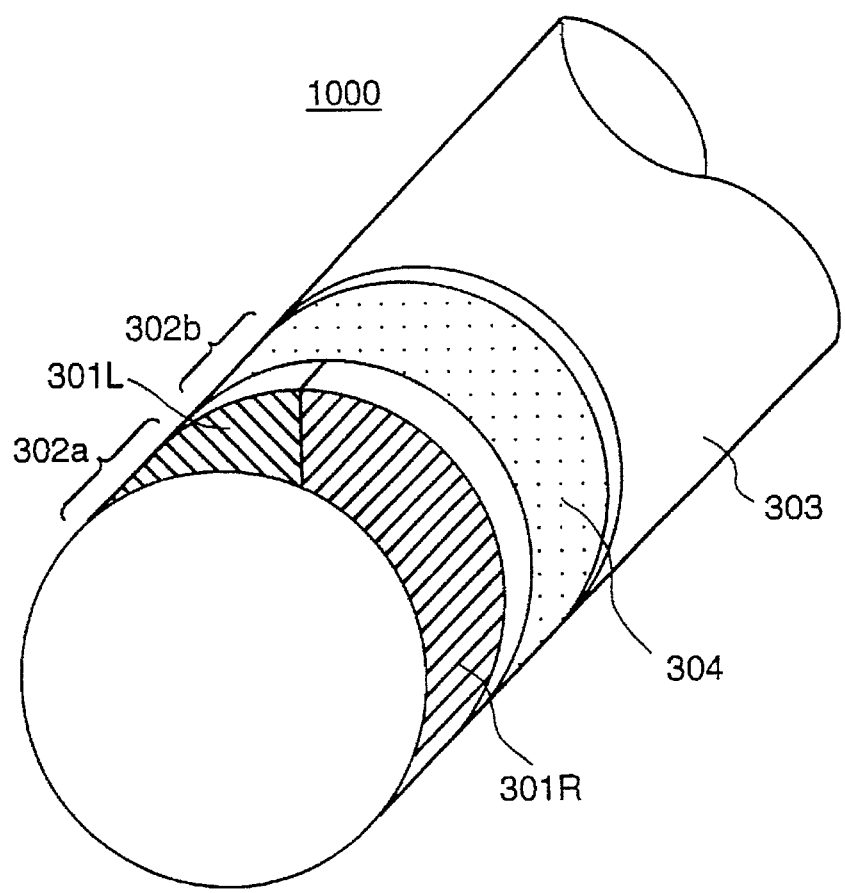
FIG. 11 is a perspective view showing the arrangement of the distal end portion of the first example of an endoscope used in the endoscope system shown in FIG. 10.
Figure 12:
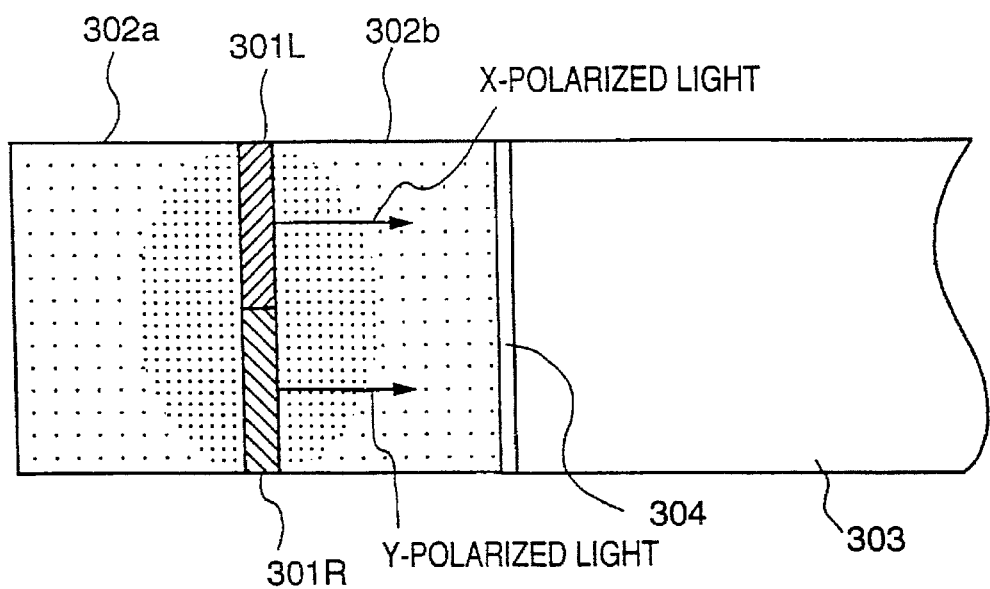
FIG. 12 is a sectional view showing the arrangement of the distal end portion of the first example of the endoscope used in the endoscope system shown in FIG. 10.

FIG. 11 is a schematic view showing the arrangement on the object side (close to the object 2000) of the image guide 103 of the endoscope according to the first example, and FIG. 12 is a schematic top view of the arrangement on the object side of the image guide 103.

Referring to FIGS. 11 and 12, reference numeral 303 denotes an image guide main body. Reference numerals 302a and 302b denote SELFOC lenses (or GRIN lenses) which are divided into two portions that sandwich a polarization filter 301 therebetween. The total length, in the longitudinal direction of the guide 103, of the lenses 302a and 302b is set so that an object image transmitted through the lens 302a is formed on an interface 304 between the lens 302b and the guide main body 303. The polarization filter 301 is divided into two portions 301L and 301R, as shown in FIGS. 11 and 12. The azimuth angles of polarization of the two filter portions 301L and 301R are right angles. For the sake of convenience, these directions are defined by X- and Y-directions. The division surface of the polarization filter portions 301L and 301R is perpendicular to the optical axis of the guide 103, and includes the optical axis. Therefore, light components transmitted through the polarization filter portions 301L and 301R are respectively X- and Y-polarized light components. More specifically, the optical images of the X- and Y-polarized light components respectively transmitted through the filter portions 301L and 301R are formed on the interface 304, and are then incident on the guide main body 303.

Therefore, in the guide main body 303, the X-polarized image light for the left eye and the Y-polarized image light for the right eye are guided while mixing with each other.

Figure 13:
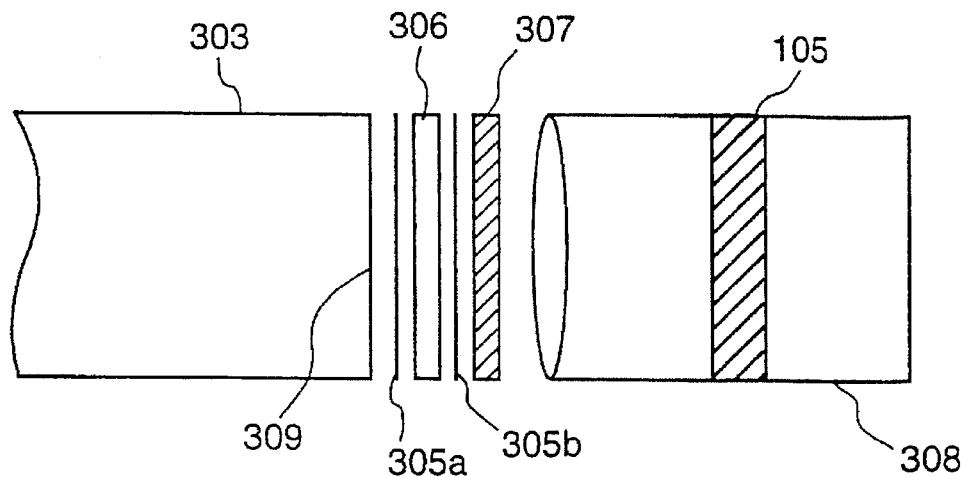
FIG. 13 is a view showing the arrangement of the proximal end portion of the first example of the endoscope.

FIG. 13 is a schematic view showing the arrangement on the image output side of the first example of the image guide 103. Referring to FIG. 13, reference numeral 309 denotes an output surface of the image guide main body 303. The two image light components input from the input surface (interface) 304 (FIG. 12) are guided along the guide main body 303, and reach the output surface 309. Transparent electrodes 305a and 305b are arranged behind the output surface 309, and a liquid crystal device 306 is arranged between these transparent electrodes 305a and 305b. An analyzer 307 is arranged behind the electrode 305b.

The liquid crystal device 306 can change its azimuth angle of polarization by controlling the voltage values to be applied to the transparent electrodes 305a and 305b. More specifically, the liquid crystal device 306, the transparent electrodes 305a and 305b, and the polarization filter 307 as the analyzer serve as a "light valve" which transmits only X-polarized light upon application of a predetermined first voltage to these electrodes, and transmits only Y-polarized light upon application of a predetermined second voltage different from the first voltage to the electrodes.

Figure 14:
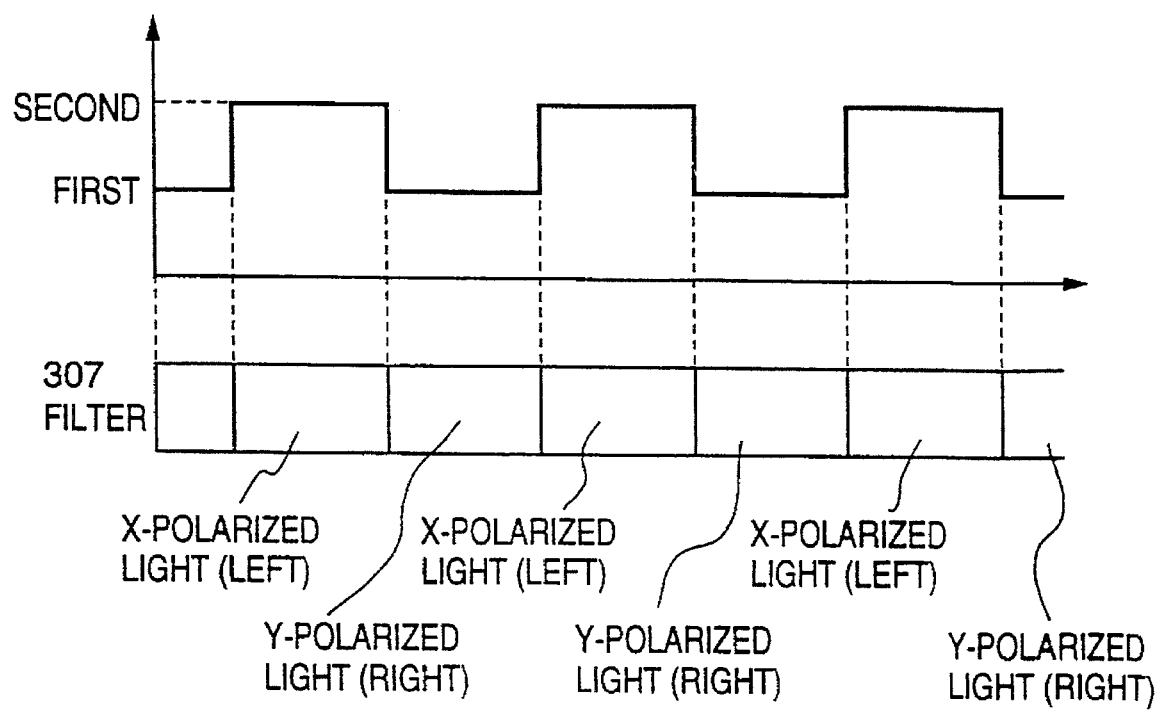
FIG. 14 is a timing chart showing control signals for the first example of the endoscope.

FIG. 14 is a timing chart showing the relationship between the timings of the first and second voltages, and the timing of output light from the polarization filter 307. More specifically, when the first and second voltages as signals from the stereoscopic image controller 113 (FIG. 10) are controlled, the filter 307 time-divisionally outputs the X-polarized light (image light for the left eye) and the Y-polarized light (image light for the right eye).

Since the time-divisional method is used, the endoscope of the first example does not require two CCDs, but requires only one CCD 115, as shown in FIG. 13. Referring to FIG. 13, reference numeral 308 denotes a television camera, which includes the CCD 115 on which an optical image is formed. The CCD 115 alternately outputs two image signals A' and B' in synchronism with synchronization signals.

The separation device 107 extracts separate image signals L and R on the basis of these image signals A' and B', as described above.

In the first example (FIG. 11), the SELFOC lenses 302a and 302b may be replaced by a normal convex lens, a Fresnel convex lens, or a combination of a plurality of lenses. The positions, sizes, and shapes of the lenses 302a and 302b, the polarization filter 301, the image guide 303 can be arbitrarily determined within the scope of the present invention. The azimuth angles of polarization of the polarization filter portions are preferably right angles. However, the present invention is not particularly limited to this as long as the two azimuth angles of polarization are different from each other.

Figure 15:
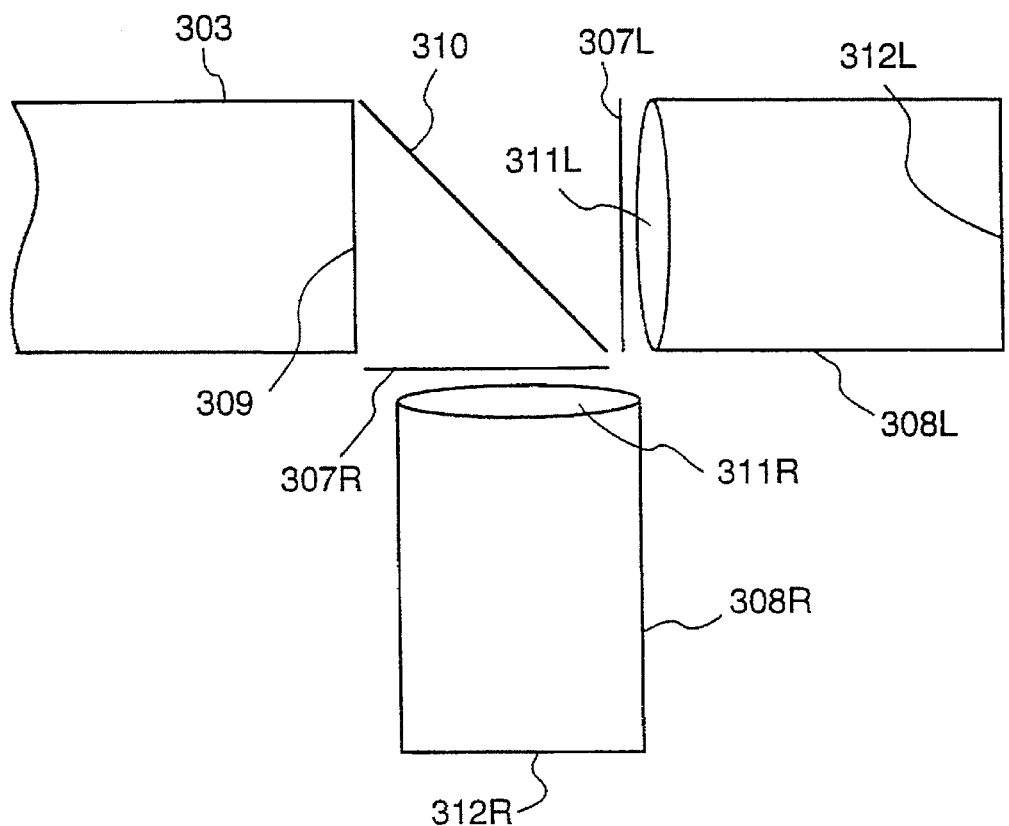
FIG. 15 is a view showing the arrangement of the proximal end portion of the second example of the endoscope used in the endoscope system shown in FIG. 10.

When the image guide of the first example is used, images for the right and left eyes are alternately generated, as shown in FIG. 14. On the other hand, it is not preferable to alternately display the images for the right and left images on the CRT 112 time-divisionally since flickering occurs. When the time-divisionally obtained images for the right and left eyes are recorded in the recorder 111, the recording efficiency is impaired. Thus, in order to convert image signals obtained using the image guide of the first example into time-parallel image signals, a known synchronization device can be used. In this case, the conversion processing from time-divisional signals into time-parallel signals may be performed prior to the "weighted difference" processing.
<Arrangement of Endoscope> . . . Second Example FIG. 15 shows the arrangement of an image guide according to the second example. Note that the second example is obtained by modifying the arrangement (FIG. 13) on the image output side of the image guide of the first example. Therefore, FIGS. 11 and 12 will be quoted for the arrangement of the object-side distal end portion of the image guide of the second example. The image guide 103 of the first example uses the time-divisional multiplexing method, while the image guide of the second example splits and simultaneously outputs image signals for the right and left eyes.

Referring to FIG. 15, a beam splitter 310 comprising, e.g., a prism, a half mirror, or the like is disposed behind the image output surface 309. The beam splitter 310 splits the mixed light of X- and Y-polarized light components from the guide main body 303 into two systems, and guides them toward polarization filters 307L and 307R.

The image guide according to the second example requires two television cameras 308L and 308R. The television camera 308L for the left eye (the television camera 308R for the right eye) has a lens 311L (lens 311R) and an imaging surface 312L (imaging surface 312R). The X-polarized light (image for the left eye) from the polarization filter 307L is imaged by the CCD 105L (see FIG. 10) arranged on the imaging surface 312L of the television camera 308L. The Y-polarized light (image for the right eye) from the polarization filter 307R is imaged by the CCD 105R (see FIG. 8) arranged on the imaging surface 312R of the television camera 308R.

The separation device 107 performs the "weighted difference" calculation according to equations (3) and (4) for the image signals imaged by the cameras 308L and 308R.

In this manner, when the image guide of the second example is used, a pair of time-parallelly continuous images (for the right and left eyes) can be completely separately obtained.

In the second example, when the beam splitter 310 has polarization selection characteristics with respect to polarized light images, the polarization filters 307L and 307R can be omitted.

Figure 16:
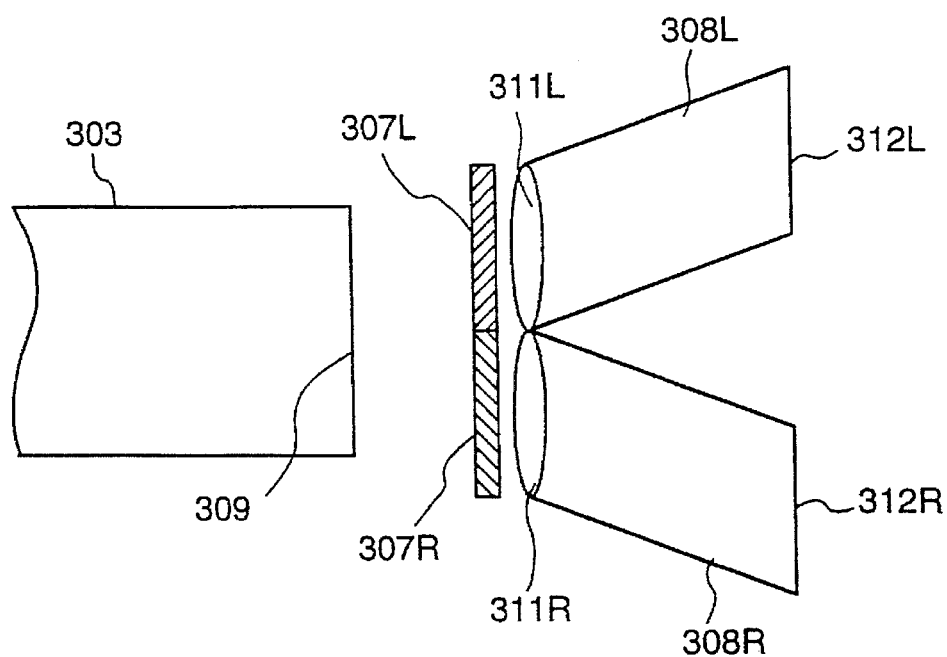
FIG. 16 is a view showing the arrangement of the proximal end portion of the third example of the endoscope used in the endoscope system shown in FIG. 10.

According to the second example, time-parallel right and left image signals can be obtained. If processing for converting the time-parallel image signals into time-divisional signals is required, the conversion processing may be executed after the "weighted difference" processing.
<Arrangement of Endoscope> . . . Third Example FIG. 16 shows the image guide of the third example. In this image guide, the beam splitter 310 is omitted from the endoscope system of the second example.

More specifically, the polarization filters 307L and 307R are juxtaposed, so that light transmitted through the guide main body is incident on the filters 307L and 307R. The television cameras 308L and 308R are respectively disposed behind the filters 307L and 307R. With this arrangement, the beam splitter can be omitted.

Figure 17:
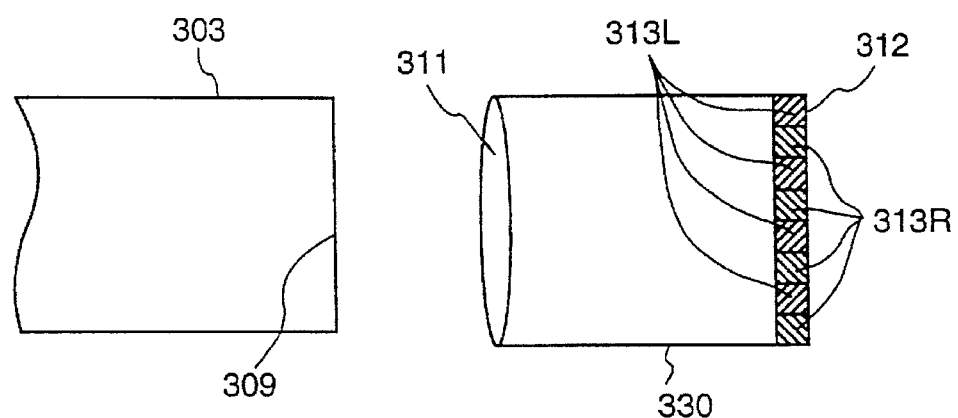
FIG. 17 is a view showing the arrangement of the proximal end portion of the fourth example of the endoscope used in the endoscope system shown in FIG. 10.

Note that the polarization filters 307L and 307R may be disposed at any positions in the range from the space before the lenses 311L and 311R to the imaging surfaces 312L and 312R.
<Arrangement of Endoscope> . . . Fourth Example FIG. 17 shows the arrangement of the image guide according to the fourth example. The same reference numerals in FIG. 17 denote substantially the same elements as in the first example (FIGS. 11 to 13).

The fourth example is different from the image guide of the second example (FIG. 15) or the third example (FIG. 16) in that the number of television cameras is one.

Figure 18:
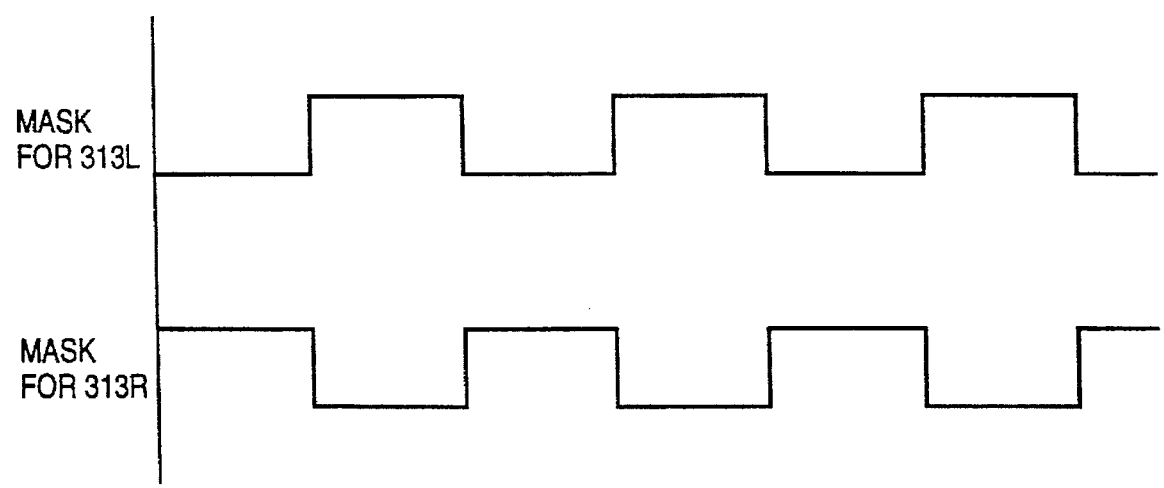
FIG. 18 is a timing chart showing control signals for the fourth example of the endoscope.

Referring to FIG. 17, polarization filters 313L and 313R having a stripe shape extending in a direction perpendicular to the plane of the drawing of FIG. 17 are adhered to an imaging surface 312 of a television camera 330. Each stripe of the polarization filters 313L and 313R has a dimension for one pixel in the up-and-down direction of FIG. 17. The polarization filters 313L and 313R have right angles as azimuth angles of polarization. Each of the polarization filters 313L and 313R has a shutter function. The shutter functions of the polarization filters 313L and 313R are time-divisionally driven in response to a mask signal (supplied from the controller 113) shown in FIG. 18. Therefore, as shown in FIG. 18, when the polarization filters 313L are masked, Y-polarized light reaches the imaging surface 312; when the polarization filters 313R are masked, X-polarized light reaches the imaging surface 312. In this manner, stereoscopic image signals are time-divisionally obtained as in the first example.

Note that the polarization filters 313L and 313R shown in FIG. 17 are adhered in a stripe pattern. However, the present invention is not limited to this, and the filters may be arbitrarily adhered as long as stereoscopic images can be obtained by a receiver.

On the other hand, an optical system for enlarging an image on the output surface 309 may be disposed between the output surface 309 of the image guide main body 303 and the television camera 330, and the positions, sizes, and shapes of the respective constituting elements may be arbitrarily determined within the scope of the present invention.

<Arrangement of Endoscope> . . . Addition of Illumination Light Guide

Figure 19:
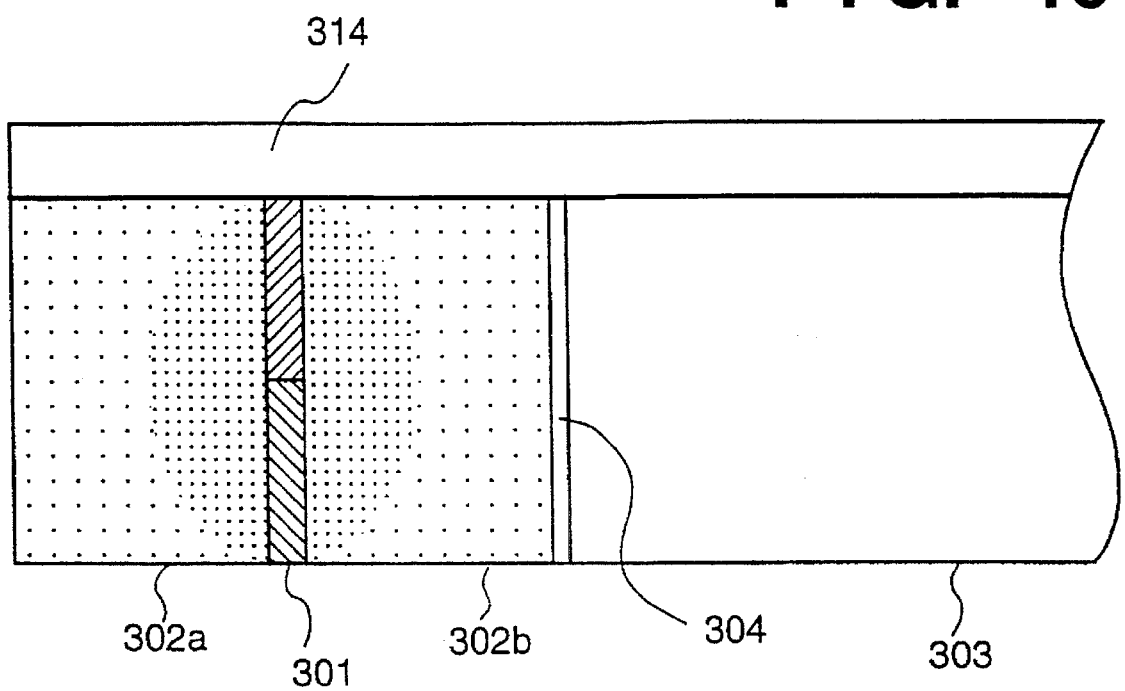
FIG. 19 is a view showing the arrangement of the fifth example of the endoscope which is obtained by adding an illumination guide to the endoscope used in the endoscope system shown in FIG. 10.

An improvement in the image guide according to the fifth example mainly relates to the structure of the distal end portion of the image guide of the first example. FIG. 19 is a schematic view showing the arrangement of the distal end portion of the image guide of the fifth example. Since the basic imaging portion in the fifth example is the same as that in the first example (FIG. 12), a description thereof will be omitted. The image guide of the fifth example is characterized by having an illumination light guide 314.

Referring to FIG. 19, the illumination light guide 314 is disposed along the guide main body 303. Since light guided by the light guide 314 is irradiated onto a monitor portion, stereoscopic viewing can be attained even in a dark place. Note that the size, shape, and position of the light guide 314 may be arbitrarily determined as long as an object can be illuminated.

<Arrangement of Endoscope> . . . Addition of Illumination Light Guide

The image guide of the fifth example (FIG. 19) is substantially the same as the sixth example since it is characterized by comprising an illumination light guide. However, the illumination light guide 314 is arranged independently of the image guide main body 303, while in the sixth example to be described below, the illumination light guide also serves as the image guide main body 303.

Figure 20:
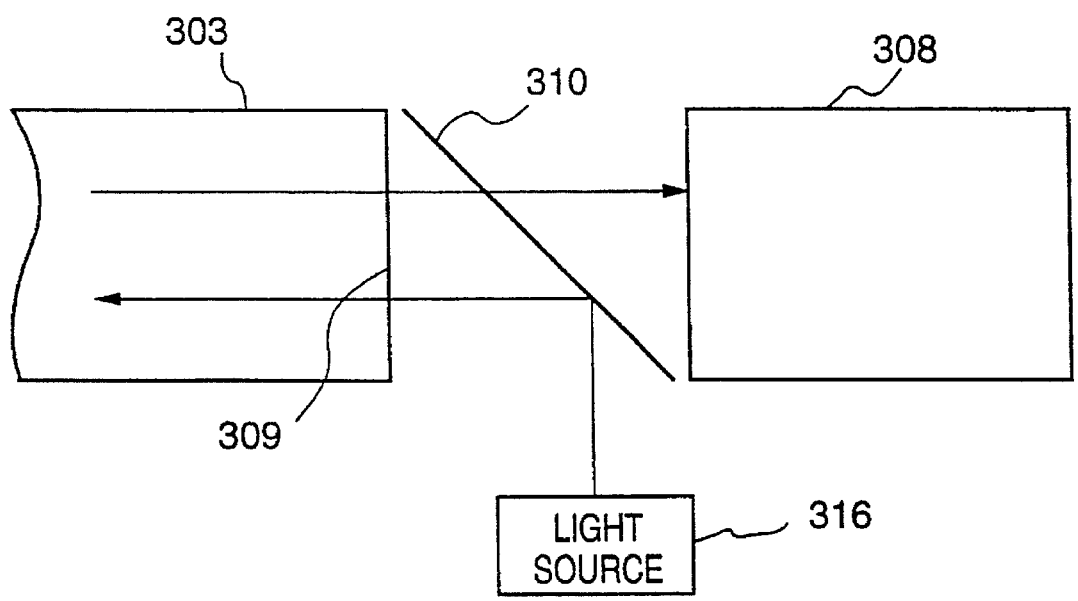
FIG. 20 is a view showing the arrangement of the sixth example of the endoscope which commonly uses, as an illumination guide, an image guide of the endoscope used in the endoscope system shown in FIG. 10.

FIG. 20 shows the arrangement of the image guide of the sixth example. Reference numeral 310 denotes a beam splitter comprising a half mirror, a prism, or the like; 308, a television camera; and 316, a light source such as a metal halide lamp. Illumination light emitted by the light source 316 is reflected by the beam splitter 310, and becomes incident into the guide main body 303. Light reflected by the object 2000 (see FIG. 10) is incident into the guide main body again, and reaches the beam splitter 303 via the guide main body 303. Polarized light transmitted through the beam splitter is incident on the camera 308.

In the sixth example as well, "weighted difference" processing is executed for image signals imaged by the camera 308 as in the first to fourth examples described above.

As described above, the guide main body of the sixth example serves as both an image guide and a light guide.

Note that the light source 316 is not limited to a white light source such as a metal halide lamp, but may comprise a light source in an infrared or ultraviolet ray range. By selecting an appropriate light source, excitation light unique to an object can be observed.

Furthermore, the positional relationship between the television camera 308 and the light source 316 is not limited to the disposition shown in FIG. 20.

Figure 21:
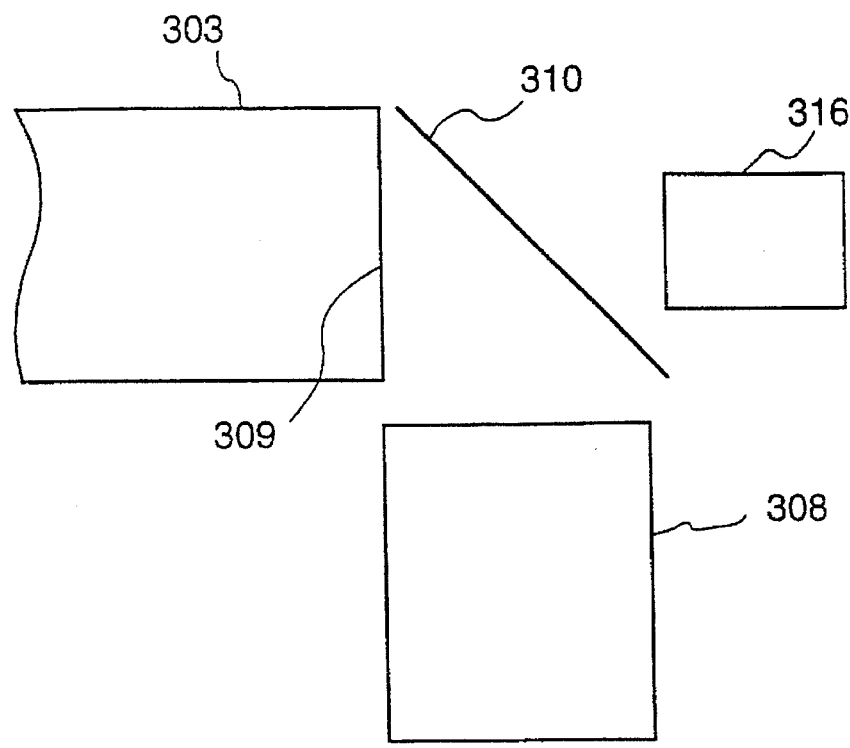
FIG. 21 is a view showing the arrangement of the first modification of the sixth example of the endoscope.
Figure 22:
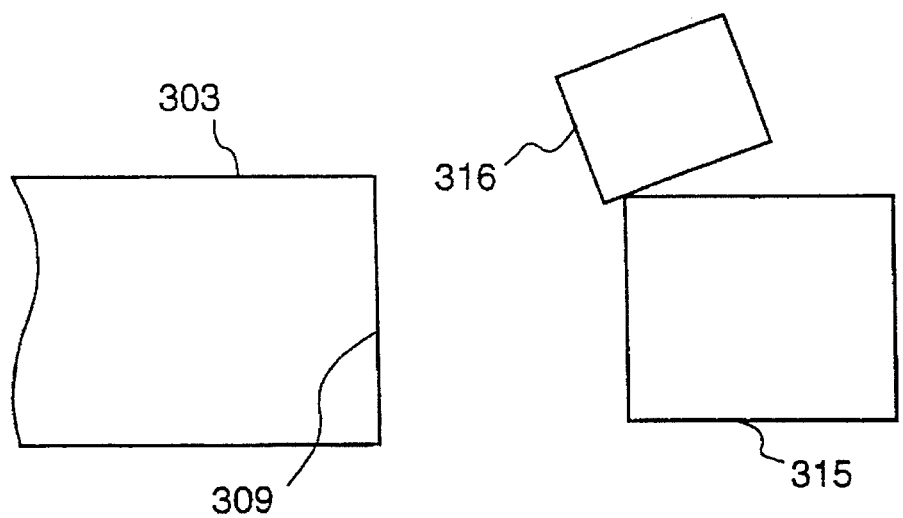
FIG. 22 is a view showing the arrangement of the second modification of the sixth example of the endoscope.

For example, as shown in FIG. 21, the positions of the television camera 308 and the light source 316 may be reversed to those in FIG. 20. Furthermore, as shown in FIG. 22, when the light source 316 is arranged aside the camera 308, the beam splitter 310 can be omitted.

Note that an optical system for enlarging an image on the output surface 309 of the image guide main body 303 may be disposed between the camera 308 and the image output surface 309.

<Arrangement of Endoscope> . . . Seventh Example

Figure 23:
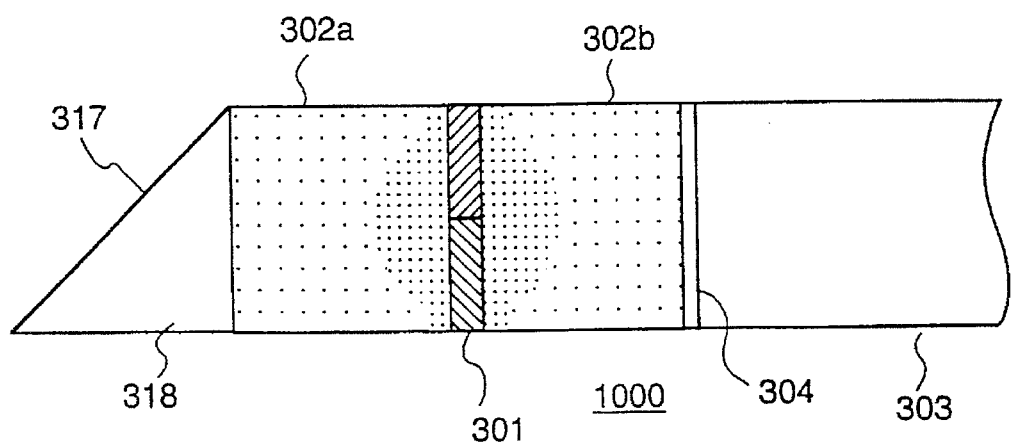
FIG. 23 is a view showing the arrangement of the seventh example of the endoscope.

The image guide of the first example is effective for imaging the object 2000 present in the longitudinal direction of the image guide main body 303, but is difficult to image an object present aside the guide 103. Thus, the image guide shown in FIG. 23 as the seventh example has a prism 318 having a mirror surface 317 at the distal end of the main body 303.

The prism 318 captures an object image present in a direction perpendicular to the longitudinal direction of the guide main body 303 (i.e., aside the guide 103), and guides it toward the lens 302.

Note that the prism need not always be arranged to capture an object image present aside the guide. For example, a mirror may be simply arranged.

<Arrangement of Endoscope> . . . Eighth Example

All the image guides according to the first to sixth examples use an optical fiber. However, the image guide of the eighth example to be described below is characterized by using a relay lens 319 in place of the optical fiber, as shown in FIG. 24.

Figure 24:
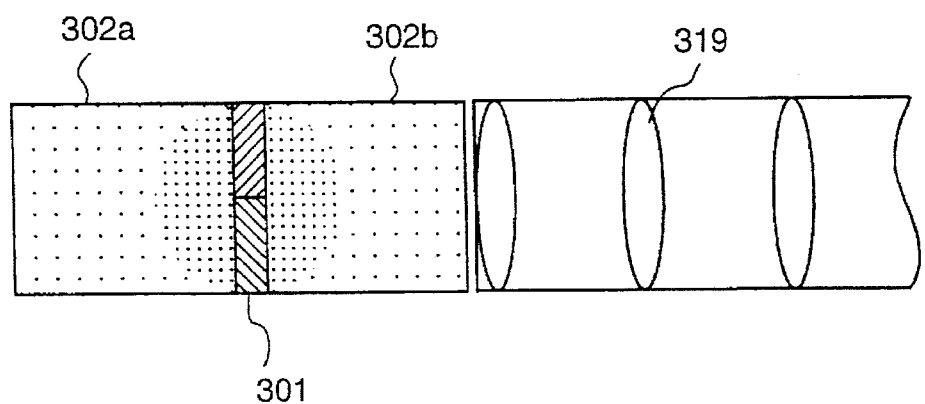
FIG. 24 is a view showing the arrangement of the eighth example of the endoscope using a relay lens system.

Referring to FIG. 24, the relay lens system 319 is disposed, so that the incident surface of the relay lens system 319 is located on the actual imaging surface of an object behind the SELFOC lens 302. With this relay lens, stereoscopic image light components having right angles as azimuth angles of polarization can also be simultaneously transmitted toward the image output side as images for the right and left images.

Note that the SELFOC lens 302 may comprise a normal convex lens, a Fresnel convex lens, or a combination of a plurality of lenses. The positions, sizes, and shapes of the lens 302, the polarization filter 301, and the relay lens system 319 may be arbitrarily determined within the scope of the present invention.

The azimuth angles of polarization of the polarization filter 301 are preferably right angles. However, the present invention is not particularly limited to this as long as the two angles are different from each other.

The arrangement on the image output side of the endoscope system having the image guide of the eighth example is the same as that (FIG. 15) of the above-mentioned endoscope system (e.g., the second example) having an image guide using an optical fiber. More specifically, stereoscopic images for the right and left eyes are split at a position behind the image output surface of the relay lens system 319, and the split images are image-sensed by the TV camera or cameras to generate time-divisional or time-parallel stereoscopic image signals. The stereoscopic image signals are input to the CRT 112, thus displaying stereoscopic images. When the stereoscopic image signals are subjected to analog or digital weighted difference processing before they are input to the CRT 112, a pair of completely separated stereoscopic images for the right and left eyes can be obtained. Note that the positions, sizes, and shapes of the relay lens system 319 and the subsequent constituting members may be arbitrarily determined within the scope of the invention.

<Arrangement of Endoscope> . . . Ninth Example

Figure 25:
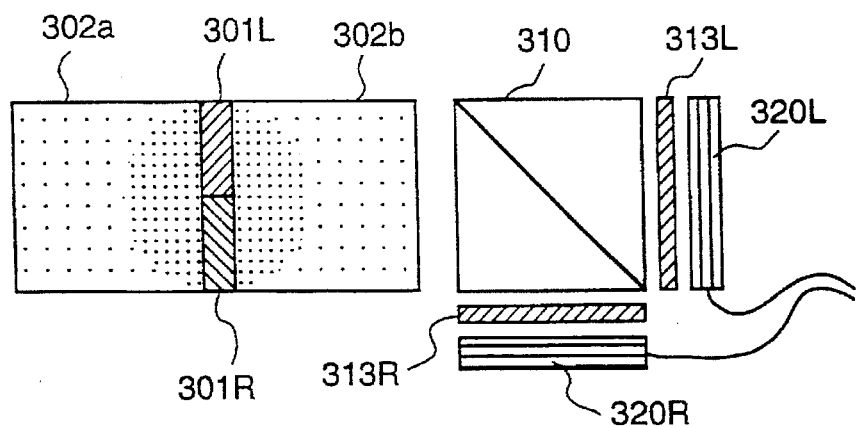
FIG. 25 is a view showing the arrangement of the eighth example of the endoscope.

FIG. 25 shows the arrangement of the image guide 103 according to the ninth example. The ninth example is characterized in that no optical fiber is used. More specifically, as shown in FIG. 25, the distal end portion of the image guide has the same structure as that of the image guide of the first example.

More specifically, the distal end portion of the image guide of the ninth embodiment has the polarization filters 301L and 301R which are arranged at or near the effective center in the optical axis direction, and have right angles as the azimuth angles of polarization, and the SELFOC lens 302 which extends along the optical axis and is divided into two regions in the longitudinal direction by a surface perpendicular to the optical axis.

The arrangement on the image output side of the image guide of the ninth example comprises the beam splitter 310 as a combination of prisms, the polarization filter 313L for transmitting X-polarized light, the polarization filter 313R for transmitting Y-polarized light, an image pickup element 320L for detecting the intensity of the X-polarized light transmitted through the polarization filter 313L, and an image pickup element 320R for detecting the intensity of the Y-polarized light transmitted through the polarization filter 313R.

Since the ninth example has no optical fiber, the image pickup elements 320L and 320R are located on the actual imaging surface of an object image behind the lens 302.

When the image guide 103 of the ninth example is used, time-divisional or time-parallel stereoscopic image signals can be generated. When the stereoscopic image signals are subjected to analog or digital weighted difference processing before they are input to the CRT, a pair of completely separated stereoscopic images for the right and left eyes can be obtained.

Upon modification of the image guide of the ninth example, the positions, sizes, and shapes of the lens 302, the polarization filters 301R and 301R, and the image pickup elements 320L and 320R may be arbitrarily determined within the scope of the present invention.

The azimuth angles of polarization of the polarization filter portions are preferably right angles. However, the present invention is not particularly limited to this as long as the two azimuth angles of polarization are different from each other.

<Arrangement of Endoscope> . . .10th Example

The first to ninth examples have the lens arrangement shown in FIG. 12. However, the lens system of the endoscope to which the present invention can be applied is not limited to the arrangement shown in FIG. 12. For example, the lens arrangement shown in FIG. 26 (10th example) may be applied.

Figure 26:
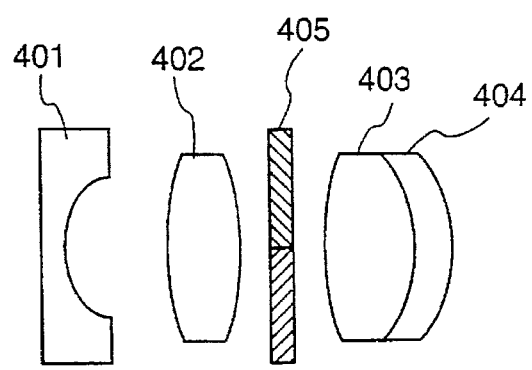
FIG. 26 is a view showing the arrangement of an optical system used in the ninth example of the endoscope.

An imaging optical system shown in FIG. 26 includes a concave lens, a convex lens, and the like (401 to 404). Note that reference numeral 405 denotes a polarization filter having the same function as that of the polarization filter 102 of the above embodiment.

The imaging optical system shown in FIG. 26 can be applied to the light-receiving system (305, 306, 307) of the first example (FIG. 13), the light-receiving system (311, 312, 330) of the fourth example (FIG. 17), the light input system (317,318) of the seventh example (FIG. 23), or the light-receiving system (310, 313,320) of the ninth example (FIG. 25).

Figure 27:
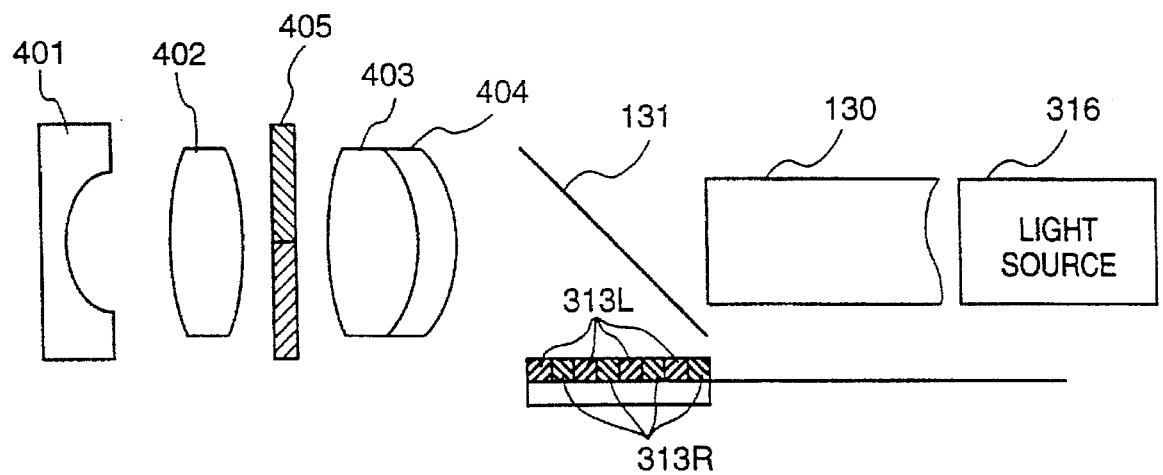
FIG. 27 is a view showing the arrangement of the 10th example of the endoscope.

FIG. 27 shows an application example of the optical system shown in FIG. 26. Referring to FIG. 27, reference numeral 130 denotes an image guide for guiding illumination light from the light source 316; 131, a beam splitter; and 313R and 313L, polarization filters.

<Improvement of Operability> . . .11th Example

The endoscope of each of all the embodiments and modifications described above has two polarization filters divided into two semi-circular portions. As described above, the positions of these two filter portions must match those of the right and left eyes of an observer. However, since the image guide itself such as a fiber is twisted, the positional relationship of lines connecting the position of the division line of the polarization filter portions and the right and left eyes may often be disturbed.

Figure 28:
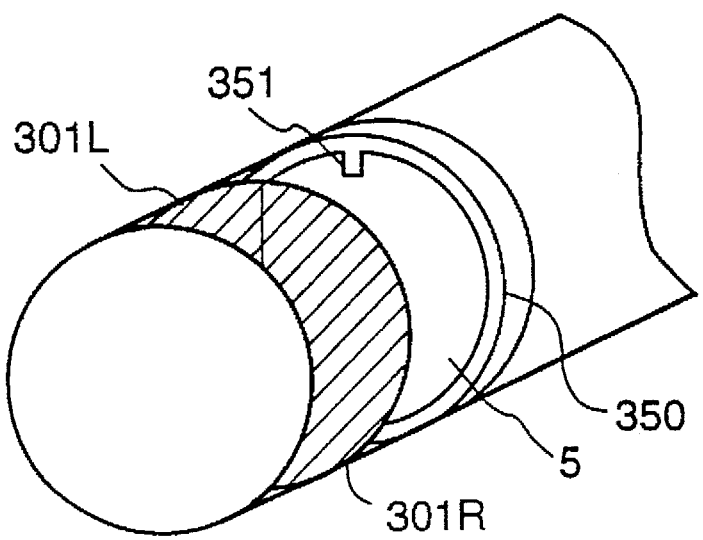
FIG. 28 is a view showing the arrangement of the 11th example of the endoscope.
Figure 29:
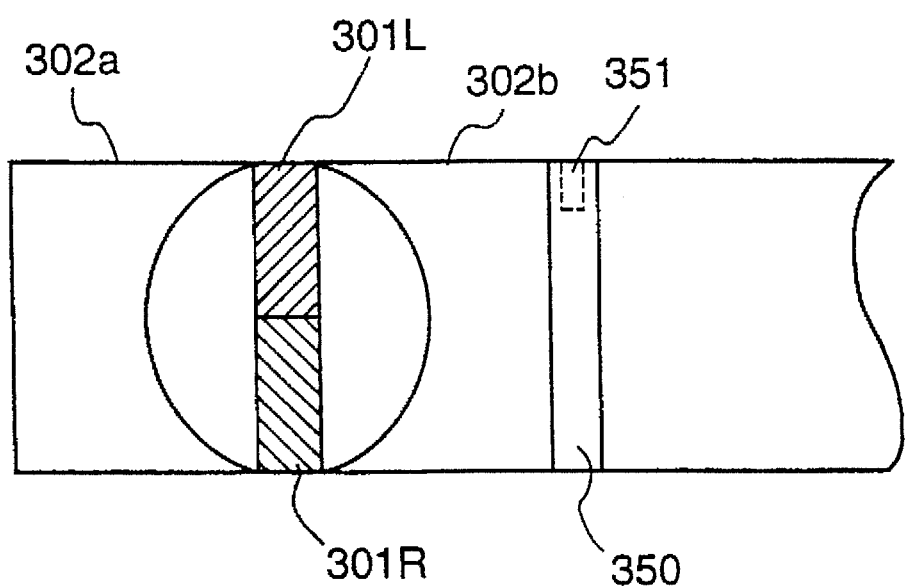
FIG. 29 is a view showing the arrangement of the 11th example of the endoscope.
Figure 30:
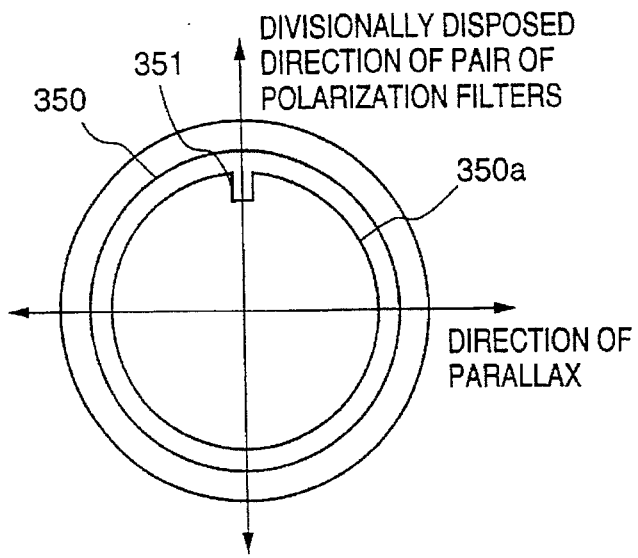
FIG. 30 is a view showing the arrangement of the 11th example of the endoscope.
Figure 31:
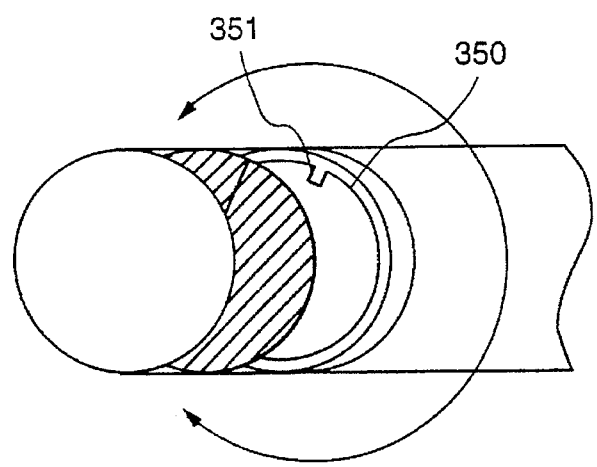
FIG. 31 is a view showing the arrangement of the 11th example of the endoscope.

The endoscope according to the 11th example (FIGS. 28, 29, and 30) is obtained by improving the endoscope of the first example shown in FIG. 13 in consideration of the above-mentioned situation. More specifically, as shown in FIGS. 28 and 29, an index ring 350 is arranged, and an index serving as a mark for the division line is formed on the ring 350. As shown in FIG. 30, the ring 350 is a hollow ring, and has a ring main body 350a as an outer circumferential surface, and a mark 351 which is opaque (or has an identifiable color) and is arranged in a direction matching the division line of the polarization filter portions. Even when the image guide is twisted, as shown in FIG. 31, since the field of view of an operator always captures the mark 351, the operator can set the positions of the right and left eyes in correspondence with the mark, thus always attaining stereoscopic viewing at the best position.

Figure 32:
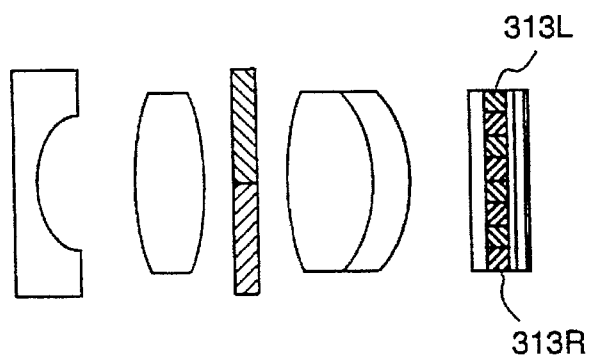
FIG. 32 is a view showing the arrangement of the 11th example of the endoscope.

Note that the ring 350 may be combined with the optical system shown in FIG. 27, as shown in FIG. 32.

As described above, according to the endoscope of the present invention, even when incident light itself is polarized, the obtained images for the right and left eyes can have substantially equal intensities by equalizing the polarization state of the incident light.

According to the image processing apparatus, the endoscope system, and the control method of the endoscope according to the present invention, two precise image data can be obtained from images obtained via a single light transmission optical member (e.g., an optical fiber) for transmitting two polarized light images having a parallax by using proportional distribution (weighted difference) processing. In other words, the proportional distribution (weighted difference) processing of the present invention allows the use of an inexpensive endoscope.

When the coefficient (a) for the proportional distribution (weighted difference) processing is determined and stored in advance, the operability of the endoscope system can be improved.

According to the image processing of the present invention, image guides (endoscopes) with various arrangements can be used.

As many apparently widely different embodiments of the present invention can be made without departing from the spirit and scope thereof, it is to be understood that the invention is not limited to the specific embodiments thereof except as defined in the appended claims.

What is claimed is:

1. An image processing apparatus comprising an optical system for transmitting first and second image light components, which have a parallax and can be separated from each other,
conversion means for converting the first and second image light components into first and second image signals; and
generation means for generating first and second image data by executing proportional distribution processing of the first and second image signals in accordance with a predetermined coefficient.

2. An apparatus according to claim 1, wherein the optical system has an optical fiber, and
the predetermined coefficient is expressed as a function of at least one of a material, diameter, and length of the optical fiber.

3. An apparatus according to claim 2, wherein the predetermined coefficient is expressed as a function of at least one of the material, diameter, and length of the optical fiber, and a pressure externally applied to the optical fiber.

4. An apparatus according to claim 1, wherein the predetermined coefficient is stored in advance in storage means as a function value defined by a shape of the optical system as a parameter.

5. An apparatus according to claim 1, wherein said conversion means comprises image pickup elements for converting the first and second image light components into the first and second image signals as electrical signals, and
said generation means comprises:
inverse conversion means for inversely converting the first and second image signals from said image pickup elements into first and second light intensity data representing light intensities; and
means for performing the proportional distribution processing of the first and second light intensity data in accordance with the predetermined coefficient.

6. An apparatus according to claim 1, wherein the first and second image light components in the optical system have substantially different polarization characteristics.

7. An apparatus according to claim 1, further comprising means for storing or displaying the first and second image data.

8. An endoscope system comprising:
an endoscope having an optical system for transmitting first and second image light components, which have a parallax and can be separated from each other;
conversion means for converting the first and second image light components into first and second image signals; and
generation means for generating first and second image data by executing proportional distribution processing of the first and second image signals in accordance with a predetermined coefficient.

9. A system according to claim 8, wherein the optical system has an optical fiber, and
the predetermined coefficient is expressed as a function of at least one of a material, diameter, and length of the optical fiber.

10. A system according to claim 9, wherein the predetermined coefficient is expressed as a function of at least one of the material, diameter, and length of the optical fiber, and a pressure externally applied to the optical fiber.

11. A system according to claim 8, wherein the predetermined coefficient is stored in advance in storage means as a function value defined by a shape of the optical system as a parameter.

12. A system according to claim 8, wherein said conversion means comprises image pickup elements for converting the first and second image light components into the first and second image signals as electrical signals, and
said generation means comprises:
inverse conversion means for inversely converting the first and second image signals from said image pickup elements into first and second light intensity data representing light intensities; and
means for performing the proportional distribution processing of the first and second light intensity data in accordance with the predetermined coefficient.

13. A system according to claim 8, wherein the first and second image light components in the optical system have substantially different polarization characteristics.

14. A system according to claim 8, further comprising means for storing or displaying the first and second image data.

15. A system according to claim 13, wherein the optical system of said endoscope comprises an optical fiber, a light input portion arranged at a distal end portion of said optical fiber, and a light output portion arranged at a proximal end portion of said optical fiber, and
said light input portion comprises a pair of filters which are arranged at or near an effective center in an optical axis direction as an aperture position of the observation lens, have different azimuth angles of polarization, and are divisionally arranged on right and left regions of a surface substantially perpendicular to the optical axis.

16. A system according to claim 15, wherein each of said pair of polarization filters has a semi-circular shape.

17. A system according to claim 13, wherein the optical system of said endoscope comprises an optical fiber, a light input portion arranged at a distal end portion of said optical fiber, and a light output portion arranged at a proximal end portion of said optical fiber, and
said light output portion comprises:
polarization axis rotation means for time-divisionally rotating axes of polarization of two polarized light images transmitted through said optical fiber; and
an analyzer arranged behind said polarization axis rotation means.

18. A system according to claim 13, wherein the optical system of said endoscope comprises an optical fiber, a light input portion arranged at a distal end portion of said optical fiber, and a light output portion arranged at a proximal end portion of said optical fiber, and
said light output portion comprises:
a beam splitter for splitting optical paths of two polarized light images transmitted through said optical fiber; and
a pair of polarization filters which respectively transmit the split polarized light images and have different azimuth angles of polarization.

19. A system according to claim 13, wherein the optical system of said endoscope comprises an optical fiber, a light input portion arranged at a distal end portion of said optical fiber, and a light output portion arranged at a proximal end portion of said optical fiber, and
said light output portion comprises a pair of polarization filters which are arranged adjacent to each other at a position near an exit of said optical fiber, and have different azimuth angles of polarization to respectively transmit two polarized light images from said optical fiber.

20. A system according to claim 13, wherein the optical system of said endoscope comprises an optical fiber, a light input portion arranged at a distal end portion of said optical fiber, and a light output portion arranged at a proximal end portion of said optical fiber, and said light output portion comprises a plurality of first polarization filters and a plurality of second polarization filters, which have different azimuth angles of polarization so as to respectively transmit two polarized light images from said optical fiber.

21. A system according to claim 13, further comprising a light guide disposed near the optical system.

22. A system according to claim 13, wherein the optical system of said endoscope comprises an optical fiber, a light input portion arranged at a distal end portion of said optical fiber, and a light output portion arranged at a proximal end portion of said optical fiber, and said light output portion comprises:

an illumination light source arranged near said light output portion; and means for guiding illumination light from said illumination light source toward said proximal end portion of said optical fiber, whereby said optical fiber serves as a bidirectional optical fiber, and is used as a light guide for illuminating an object.

23. A system according to claim 13, wherein the optical system of said endoscope comprises an optical fiber, a light input portion arranged at a distal end portion of said optical fiber, and a light output portion arranged at a proximal end portion of said optical fiber, and the optical system further comprises an image reflection member at a distal end of said light input portion.

24. A system according to claim 23, wherein said image reflection member comprises one of a mirror surface and a prism having a mirror surface.

25. A system according to claim 13, wherein said optical system comprises an imaging member.

26. A system according to claim 13, wherein the optical system of said endoscope comprises a light transmission path consisting of a relay lens, a light input portion arranged at a distal end side of said light transmission path, and a light output portion arranged at a proximal end side of said light transmission path.

27. A system according to claim 13, further comprising a pair of solid-state image pickup elements arranged behind the optical system of said endoscope.

28. A method of controlling an endoscope having an optical system for transmitting first and second image light components, which have a parallax and can be separated from each other, comprising the steps of:

converting the first and second image light components into first and second image signals by controlling image pickup elements; and generating first and second image data by performing proportional distribution processing of the first and second image signals on the basis of conversion characteristics of the image pickup elements and a predetermined coefficient representing a shape of the optical system.

29. A method according to claim 28, wherein the predetermined coefficient is stored as a value corresponding to a geometric shape of the optical system.

* * * * *

UNITED STATES PATENT AND TRADEMARK OFFICE
CERTIFICATE OF CORRECTION

PATENT NO. : 5,649,897
DATED : July 22, 1997
INVENTOR(S) : Toshihisa NAKAMURA et al It is certified that error appears in the above-identified patent and that said Letters Patent is hereby corrected as shown below:

In Column 22, line 66, after "comprising" insert -- : --.

Signed and Sealed this

Twenty-fifth Day of November, 1997

Attest:

BRUCE LEHMAN

Attesting Officer                Commissioner of Patents and Trademarks